United States Patent
Fu et al.

(10) Patent No.: US 7,840,093 B2
(45) Date of Patent: *Nov. 23, 2010

(54) IMAGE ENHANCEMENT METHOD AND SYSTEM FOR FIDUCIAL-LESS TRACKING OF TREATMENT TARGETS

(75) Inventors: Dongshan Fu, Santa Clara, CA (US); Gopinath Kuduvalli, San Jose, CA (US)

(73) Assignee: Accuray, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/334,789

(22) Filed: Dec. 15, 2008

(65) Prior Publication Data

US 2009/0091567 A1    Apr. 9, 2009

Related U.S. Application Data

(62) Division of application No. 10/881,208, filed on Jun. 30, 2004, now Pat. No. 7,522,779.

(51) Int. Cl.
*G06K 9/32* (2006.01)

(52) U.S. Cl. ...................... 382/294; 382/254

(58) Field of Classification Search .................. 382/254
See application file for complete search history.

(56) References Cited

U.S. PATENT DOCUMENTS

| | | | |
|---|---|---|---|
| 4,029,963 A | | 6/1977 | Alvarez et al. |
| 4,438,495 A | | 3/1984 | Collins et al. |
| 4,641,352 A | | 2/1987 | Fenster et al. |
| 5,117,829 A | | 6/1992 | Miller et al. |
| 5,297,036 A | | 3/1994 | Grimaud |
| 5,297,037 A | * | 3/1994 | Ifuku ........................... 378/8 |
| 5,563,962 A | * | 10/1996 | Peters et al. ................. 382/261 |
| 5,611,000 A | | 3/1997 | Szeliski et al. |
| 5,644,406 A | * | 7/1997 | Harrington et al. .......... 382/239 |

(Continued)

OTHER PUBLICATIONS

Penney et al., A Comparison of Similarity Measures for Use in 2D-3D Medical Image Registration, Aug. 1998, IEEE Transactions on Medical Imaging, vol. 17, No. 4, pp. 586-595.

(Continued)

*Primary Examiner*—Vu Le
*Assistant Examiner*—Tsung-Yin Tsai
(74) *Attorney, Agent, or Firm*—Blakely, Sokoloff, Taylor & Zafman LLP

(57) ABSTRACT

A method and system are presented for enhancing one or more images of an object, so as to increase the visibility within the images of one or more structures within the object. The object may be an anatomical region of a patient, and may include one or more reference structures, for example skeletal structures or vertebral structures, and one or more treatment targets, for example tumors or lesions. An operator, for example a top-hat filter operator, selects at least a first neighborhood and a second neighborhood within the images. The operator selects within each neighborhood one or more pixels having an optimal pixel value, and eliminates the remaining pixels in these neighborhoods. When the operator is applied to the selected neighborhoods, only the pixels having the greatest pixel values remain in the selected neighborhoods, and the remaining pixels are eliminated in the selected neighborhoods. As a result, desired features can be located and enhanced in the images.

10 Claims, 29 Drawing Sheets

U.S. PATENT DOCUMENTS

| | | | |
|---|---|---|---|
| 5,687,303 A * | 11/1997 | Motamed et al. | 358/1.18 |
| 5,696,848 A | 12/1997 | Patti et al. | |
| 5,825,908 A | 10/1998 | Pieper et al. | |
| 5,835,618 A | 11/1998 | Fang et al. | |
| 5,901,199 A | 5/1999 | Murphy et al. | |
| 5,987,164 A | 11/1999 | Szeliski et al. | |
| 6,006,013 A * | 12/1999 | Rumph et al. | 358/1.15 |
| 6,081,577 A | 6/2000 | Webber | |
| 6,235,038 B1 | 5/2001 | Hunter | |
| 6,239,829 B1 * | 5/2001 | Curry | 347/251 |
| 6,256,104 B1 * | 7/2001 | Rumph et al. | 358/1.15 |
| 6,262,740 B1 | 7/2001 | Lauer et al. | |
| 6,295,377 B1 | 9/2001 | Dufaux et al. | |
| 6,307,914 B1 | 10/2001 | Kunieda et al. | |
| 6,411,733 B1 * | 6/2002 | Saund | 382/190 |
| 6,415,013 B1 | 7/2002 | Hsieh et al. | |
| 6,470,207 B1 | 10/2002 | Simon et al. | |
| 6,490,476 B1 | 12/2002 | Townsend et al. | |
| 6,501,981 B1 | 12/2002 | Schweikard | |
| 6,504,541 B1 | 1/2003 | Liu | |
| 6,516,046 B1 | 2/2003 | Frohlich et al. | |
| 6,549,576 B1 | 4/2003 | Moriyoshi | |
| 6,549,645 B1 | 4/2003 | Oikawa et al. | |
| 6,658,059 B1 | 12/2003 | Iu et al. | |
| 6,662,036 B2 | 12/2003 | Cosman | |
| 6,665,450 B1 | 12/2003 | Cornog et al. | |
| 6,665,555 B2 | 12/2003 | Henderson | |
| 6,728,401 B1 * | 4/2004 | Hardeberg | 382/167 |
| 6,728,424 B1 | 4/2004 | Zhu et al. | |
| 6,757,423 B1 | 6/2004 | Amini | |
| 6,782,287 B2 | 8/2004 | Grzeszczuk | |
| 6,792,158 B1 | 9/2004 | Brumley | |
| 6,792,162 B1 | 9/2004 | Edgar | |
| 6,837,892 B2 | 1/2005 | Shoham | |
| 6,907,281 B2 | 6/2005 | Grzeszczuk | |
| 7,024,237 B1 | 4/2006 | Bova | |
| 7,072,435 B2 | 7/2006 | Metz et al. | |
| 7,187,792 B2 | 3/2007 | Fu et al. | |
| 7,204,640 B2 | 4/2007 | Fu et al. | |
| 7,231,076 B2 | 6/2007 | Fu et al. | |
| 7,327,865 B2 | 2/2008 | Fu et al. | |
| 7,330,578 B2 | 2/2008 | Wang | |
| 7,366,278 B2 | 4/2008 | Fu et al. | |
| 7,397,890 B2 * | 7/2008 | Sukovic et al. | 378/38 |
| 7,426,318 B2 | 9/2008 | Fu et al. | |
| 7,480,399 B2 | 1/2009 | Fu et al. | |
| 2002/0038118 A1 | 3/2002 | Shoham | |
| 2002/0077543 A1 | 6/2002 | Grzeszczuk et al. | |
| 2002/0191814 A1 * | 12/2002 | Ellis et al. | 382/103 |
| 2003/0011624 A1 | 1/2003 | Ellis | |
| 2003/0025945 A1 * | 2/2003 | Rumph et al. | 358/426.13 |
| 2003/0035592 A1 | 2/2003 | Cornog et al. | |
| 2003/0065260 A1 | 4/2003 | Cheng et al. | |
| 2003/0072479 A1 | 4/2003 | Totterman et al. | |
| 2003/0073901 A1 | 4/2003 | Simon et al. | |
| 2003/0112921 A1 * | 6/2003 | Lang et al. | 378/54 |
| 2003/0176780 A1 | 9/2003 | Arnold | |
| 2003/0228044 A1 | 12/2003 | Gopalasamy et al. | |
| 2004/0005089 A1 * | 1/2004 | Robles et al. | 382/141 |
| 2004/0030246 A1 | 2/2004 | Townsend et al. | |
| 2004/0042656 A1 | 3/2004 | Timor et al. | |
| 2004/0042662 A1 | 3/2004 | Wilensky et al. | |
| 2004/0052409 A1 | 3/2004 | Bansal et al. | |
| 2004/0091170 A1 | 5/2004 | Cornog et al. | |
| 2004/0092815 A1 | 5/2004 | Schweikard et al. | |
| 2004/0101086 A1 | 5/2004 | Sabol et al. | |
| 2004/0131150 A1 | 7/2004 | Pankratov | |
| 2004/0228453 A1 | 11/2004 | Dobbs et al. | |
| 2004/0234113 A1 | 11/2004 | Miga | |
| 2004/0240733 A1 | 12/2004 | Hobson et al. | |
| 2004/0263878 A1 * | 12/2004 | McElvain | 358/1.9 |
| 2004/0267113 A1 | 12/2004 | Thomson | |
| 2005/0018889 A1 | 1/2005 | Li | |
| 2005/0047544 A1 | 3/2005 | Fu | |
| 2005/0049477 A1 | 3/2005 | Fu | |
| 2005/0049478 A1 | 3/2005 | Kuduvalli | |
| 2005/0078881 A1 | 4/2005 | Xu et al. | |
| 2005/0238223 A1 | 10/2005 | Guhring | |
| 2005/0272991 A1 | 12/2005 | Xu et al. | |
| 2005/0288578 A1 * | 12/2005 | Durlak | 600/434 |
| 2006/0002601 A1 | 1/2006 | Fu | |
| 2006/0002615 A1 | 1/2006 | Fu et al. | |
| 2006/0002630 A1 | 1/2006 | Fu et al. | |
| 2006/0257045 A1 * | 11/2006 | McCandlish | 382/261 |
| 2007/0103731 A1 * | 5/2007 | Tse et al. | 358/3.27 |
| 2008/0013125 A1 * | 1/2008 | McElvain | 358/2.1 |
| 2008/0049238 A1 * | 2/2008 | Nagarajan et al. | 358/1.9 |
| 2008/0068660 A1 * | 3/2008 | Loce et al. | 358/3.06 |

OTHER PUBLICATIONS

Coste-Maniere, E., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

F. Wang et al., "Cumulative Residual Entropy, A New Measure of Information & Its Application to Image Alignment", Proceedings of the Ninth IEEE International Conference of Computer Vision (ICCV '03), 2003 IEEE.

Josien P.W. Pluim et al., "Mutual Information Based Registration of Medical Images: A Survey", IEEE Transactions on Medical Imaging, vol. XX, No. Y, 2003.

Van de Casteele, E. et al., "An Energy-based Beam Hardening Model in Tomography, Physics in medicine and Biology", Nov. 12, 2002, vol. 47, No. 23, pp. 4181-4190.

Daniel B. Russakoff, et al., "Fast Calculation of Digitally Reconstructed Radiographs Using Light Fields", 12 pp (684-695), Medical Imaging 2003: Image Proceeding, Milan Sonka, J. Michael Fitzpatrick, Editors, Proceedings of SPIE vol. 5032 (2003) © 2003 SPIE.

International Preliminary Report on Patentability, PCT/US2005/011200, filed Apr. 1, 2005, mailed Jan. 18, 2007.

PCT International Search Report, PCT/US2005/008617, filed Mar. 14, 2005, mailed Sep. 21, 2006.

PCT Written Opinion of the International Searching Authority, PCT/US2005/008617, filed Mar. 14, 2005, mailed Sep. 21, 2006.

Chapter I International Preliminary Report on Patentability, PCT/US2005/008617, filed Mar. 14, 2005, mailed Jan. 18, 2007.

PCT International Search Report and Written Opinion of the International Searching Authority, International Application No. PCT/US05/10754, International filing date Mar. 30, 2005, mailed Nov. 14, 2006.

PCT International Search Report and Written Op0inion, International Application No. PCT/US05/08659, International filing date Mar. 15, 2005, mailed Sep. 27, 2006, 10 pages.

PCT International Search Report and Written Opinion, PCT/US05/11200, International filing date Apr. 1, 2005, mailing date Oct. 23, 2006, 10 pages.

PCT International Search Report and Written Opinion of the International Searching Authority, PCT/US05/09485 filed Mar. 18, 2005, mailed Sep. 23, 2008.

A. Movafeghi, "Quality Improvement of Digitized Radiographs by Filtering Technique Development based on Morphological Transformations", Jul. 2004, IEEE, pp. 1845-1849.

Wein, Intensity Based Rigid 2D-3D Registration Algorithms for Radiation Therapy, Dec. 15, 2003, Technische Universitat Munchen, Fakultat fur Informatik, Doctoral Dissertation, 100 pages.

McKetty, The AAPM/RSNA Physics Tutorial for Residents, 1998, RadioGraphics, vol. 18, pp. 151-163.

Seibert et al., X-ray Imaging Physics for Nuclear Medicine Technologists Part 2: X-ray Interactions and Image Formation, Mar. 2005, Journal of Nuclear Medical Technology, vol. 33, No. 1, pp. 3-18.

Hubbell et al., Tables of X-ray Mass Attenuation Coefficients and Mass Energy-Absorption Coefficients, available at http://physics.nist.gov/PhysRefData/XrayMassCoef/tab4.html.

Dong et al., An image correlation procedure for digitally reconstructed radiographs and electronic portal images, 1995, International Journal of Radiation Oncology Biology Physics, vol. 33, Issue 5, pp. 1053-1060.

Gilhuijs et al., Automatic on-line inspection of patient setup in radiation therapy using electronic portal images, 1993, Medical Physics, vol. 20, No. 3, pp. 667-677.

Mansson, Patient positioning correction strategies in radiotherapy: A portal imaging study, 2004, Lund University, Department of Medical Radiation Physics, The Jubileum Institute, Masters of Science Thesis, Document No. LUJI-RADFY-EX-Jan. 2004, 35 pages.

Graeme P. Penny et al., "Validation of a two- to three-dimensional registration algorithm for aligning preoperative CT images and intraoperative fluoroscopy images," *Med. Phys.* 28(6), 1024-1032, Jun. 2001.

D. Sarrut, "Patient positioning in radiotherapy by registration of 2D portal to 3D CT images by a contend based research with similarity measures," *CARS 2000*, 707-712.

Martin J. Murphy, An automatic six-degree-of-freedom image registration algorithm for image-guided frameless stereotaxic radiosurgery, *Med. Phys.* 24(6), 857-866, Jun. 1997.

* cited by examiner $d2=(d1+d3)/2$
$d4=(d1+d7)/2$
$d5=(d1+d3+d7+d9)/4$
$d6=(d3+d9)/2$
$d8=(d7+d9)/2$

FIG. 12

| Patient | Type | Target #1 | Target #2 | Target #3 | Target #4 | Target #5 | mean |
|---|---|---|---|---|---|---|---|
| 1 | cervical | 1.03 | 0.20 | 1.00 | 0.37 | 0.53 | 0.63 |
| 2 | cervical | 0.49 | 1.05 | | | | 0.77 |
| 3 | thoracic | 0.54 | 0.45 | 0.20 | 0.31 | | 0.37 |
| 4 | thoracic | 0.48 | 0.25 | 0.41 | 0.51 | | 0.41 |
| 5 | lumbar | 0.32 | 0.61 | 0.18 | 0.90 | | 0.50 |
| 6 | lumbar | 0.33 | 0.21 | 0.25 | 0.18 | 0.71 | 0.33 |
| 7 | lumbar | 0.32 | 0.28 | 0.69 | 0.76 | | 0.51 |
| 8 | lumbar | 0.65 | 0.31 | 0.31 | 0.53 | | 0.45 |

The total mean = 0.50 mm

FIG. 18

| Patient | Type | Target #1 | Target #2 | Target #3 | Target #4 | Target #5 | mean |
|---|---|---|---|---|---|---|---|
| 1 | cervical | 1.03 | 0.55 | 0.96 | 0.36 | 0.50 | 0.67 |
| 2 | cervical | 0.80 | 0.97 | | | | 0.89 |
| 3 | thoracic | 0.62 | 0.41 | 0.27 | 0.21 | | 0.38 |
| 4 | thoracic | 0.49 | 0.32 | 0.42 | 0.39 | | 0.41 |
| 5 | lumbar | 0.25 | 0.76 | 0.61 | 1.00 | | 0.65 |
| 6 | lumbar | 0.50 | 0.31 | 0.14 | 0.18 | 0.65 | 0.35 |
| 7 | lumbar | 0.24 | 0.24 | 0.60 | 0.63 | | 0.43 |
| 8 | lumbar | 0.46 | 0.24 | 0.37 | 0.48 | | 0.39 |

The total mean = 0.52 mm

FIG. 19

IMAGE ENHANCEMENT METHOD AND SYSTEM FOR FIDUCIAL-LESS TRACKING OF TREATMENT TARGETS

REFERENCE TO RELATED APPLICATION

This application is a divisional of application Ser. No. 10/881,208, filed Jun. 30, 2004.

TECHNICAL FIELD

Embodiments of the present invention relate to the field of image enhancement.

BACKGROUND

In image registration, an optimal transformation is sought between different image acquisitions of one or more objects. Image registration techniques may be used in the medical field to relate a pre-operative image of a patient's anatomy to a near real time image of the patient during actual treatment. During radiosurgery, for example, the change in target position at the time of treatment, as compared to its position at the time of the diagnostic treatment planning, may be detected. This may be accomplished by registering the 2D image acquired at treatment time with the 3D scan obtained at the time of treatment planning. A robust and accurate 2D-3D image registration algorithm may enable the position of the target, as viewed in the real-time 2D image, to be properly correlated with the pre-operative 3D scan. In practice, a formal mathematical transformation may be derived that best aligns the pre-operative image coordinate system with the patient's physical world coordinate system, defined for example in the treatment room.

Fiducial markers may be attached to, or implanted within, the patient before the pre-operative images are acquired, in order to accomplish a point-based alignment of the different coordinate systems. These fiducial markers are typically designed so that they can be localized relatively accurately in the pre-operative image, as well as in the real physical world. The respective localization points may then be used to calculate a rigid body transformation between the two coordinate systems.

Fiducials tracking can be difficult for the patient, however, for a number of reasons. For example, high accuracy tends to be achieved by using bone-implanted fiducial markers, but less invasive techniques such as skin-attached markers or anatomical positions tend to be less accurate. Implantation of fiducials into a patient may be painful and difficult, especially for the C-spine, the implantation process for which may frequently lead to clinical complications. Attempts have therefore been made to develop techniques for fiducial-less tracking.

By using anatomical structures, for example skeletal or vertebral structures, as reference points, the need for fiducial markers (and ensuing surgical implantation) may be eliminated in image-guided surgery.

While fiducial-less tracking that relies on skeletal structures may overcome many of the drawbacks associated with implanted fiducials, these skeletal structures may frequently not be easily visible, or may even be hidden, in the pre-operative images, as well as in the real-time projection images.

Accordingly, there is a need for image enhancement techniques that can increase the contrast and bring out the details of these reference structures in image-guided surgery, both in the pre-operative images as well as in the real-time projection images.

BRIEF DESCRIPTION OF THE DRAWINGS

In FIGS. 8A and 8B, the similarity measure functions are plotted with respect to translations in two mutually orthogonal directions (x- and y-).

FIG. 12 schematically illustrates the passing on of node estimation, from a course mesh resolution level onto a finer mesh resolution level.

FIG. 18 is a table of TRE (target registration error) values for different targets located within the cervical, thoracic, and lumbar regions, in embodiments in which fiducials are used.

FIG. 19 is a table of TRE (target registration error) values for different targets located within the cervical, thoracic, and lumbar regions, in embodiments in which fiducials are removed in CT data.

DETAILED DESCRIPTION

Figure 1A:
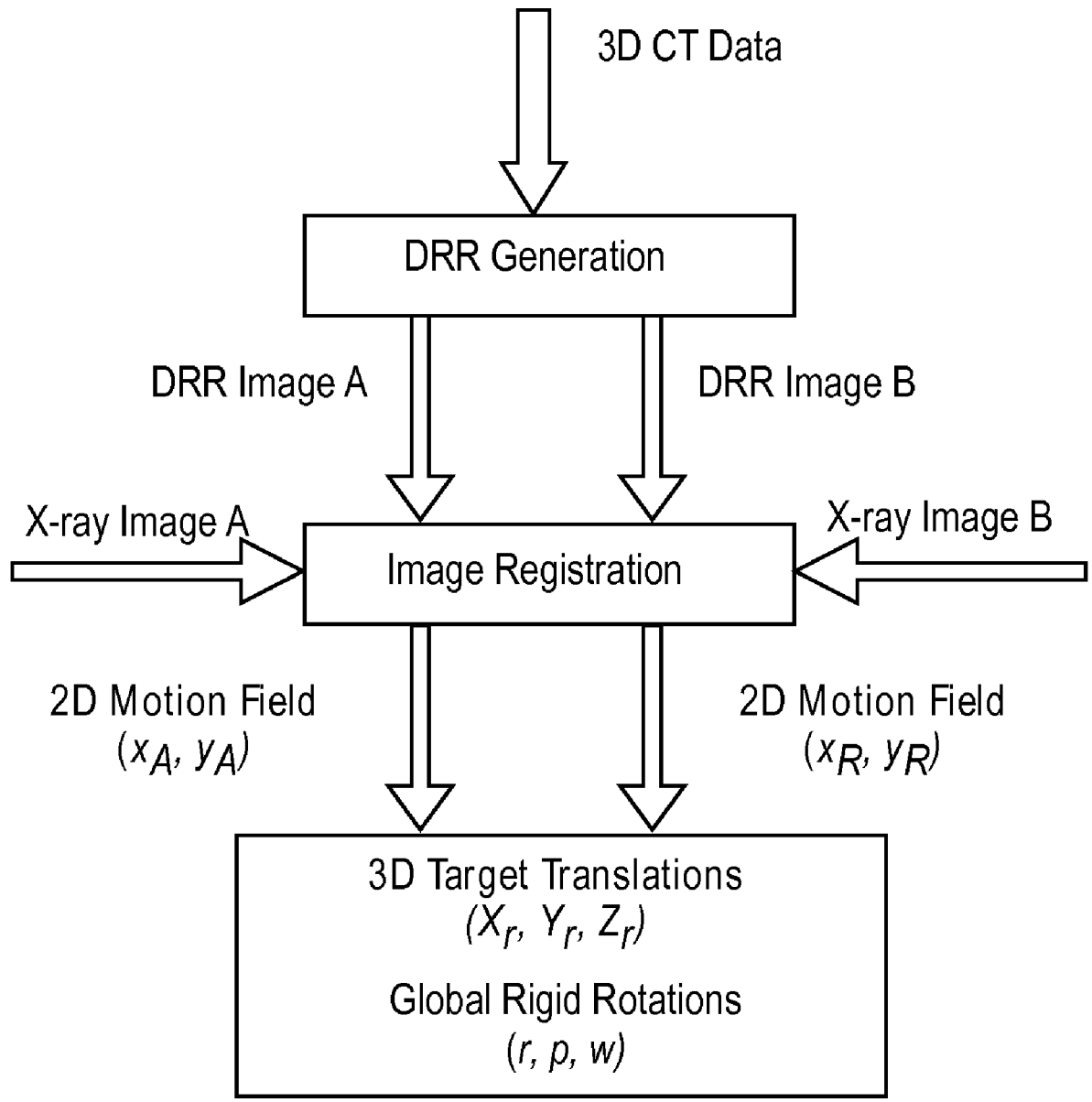
FIG. 1A provides an overall schematic block diagram of a fiducial-less tracking method and system.

A method and system is presented for tracking and aligning a treatment target, without using fiducial markers. An intensity-based, non-rigid 2D-3D image registration method and system is performed. Anatomical reference structures, for example skeletal or vertebral structures that are rigid and easily visible in diagnostic x-ray images, are used as reference points, eliminating the need for fiducial markers which must be surgically implanted. The tracking method and system of the present invention is useful in image guided radiosurgery and radiotherapy, and is particularly useful for spinal applications, i.e. for tracking skeletal structures in the body, especially in the regions containing or located close to spinal vertebrae. The method and system of the present invention, however, can also be used in any other application in which there is a need to register one image onto a different image.

In the following description, for purposes of explanation, numerous specific details are set forth in order to provide a thorough understanding of the present invention. It will be evident, however, to one skilled in the art that the present invention may be practiced without these specific details. In some instances, well-known structures and devices are shown in block diagram form, rather than in detail, in order to avoid obscuring the present invention. These embodiments are described in sufficient detail to enable those skilled in the art to practice the invention, and it is to be understood that other embodiments may be utilized and that logical, mechanical, electrical and other changes may be made without departing from the scope of the present invention.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of acts leading to a desired result. The acts are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention can be implemented by an apparatus for performing the operations herein. This apparatus may be specially constructed for the required purposes, or it may comprise a general purpose computer, selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method. For example, any of the methods according to the present invention can be implemented in hard-wired circuitry, by programming a general purpose processor or by any combination of hardware and software. One of skill in the art will immediately appreciate that the invention can be practiced with computer system configurations other than those described below, including hand-held devices, multiprocessor systems, microprocessor-based or programmable consumer electronics, network PCs, minicomputers, mainframe computers, and the like. The invention can also be practiced in distributed computing environments where tasks are performed by remote processing devices that are linked through a communications network. The required structure for a variety of these systems will appear from the description below.

The methods of the invention may be implemented using computer software. If written in a programming language conforming to a recognized standard, sequences of instructions designed to implement the methods can be compiled for execution on a variety of hardware platforms and for interface to a variety of operating systems. In addition, the present invention is not described with reference to any particular programming language. It will be appreciated that a variety of programming languages may be used to implement the teachings of the invention as described herein.

Furthermore, it is common in the art to speak of software, in one form or another (e.g., program, procedure, application . . . ), as taking an action or causing a result. Such expressions are merely a shorthand way of saying that execution of the software by a computer causes the processor of the computer to perform an action or produce a result.

For radiosurgical treatment of tumorous targets, the task of fiducial-less tracking is to predict patient target movement between pre-operative patient CT scanning and patient radiation treatment, based on the skeletal structures. Target movement is tracked by comparing the pre-operative 3D CT data and intra-operative x-ray 2D projection images, i.e. a 2D/3D image registration is performed. As well known, the basic problem in image registration is to find the optimal transformation that relates different representations or images of the same object. A 2D/3D registration, in particular, seeks to determine a projection mapping or transformation, from a 3D to a 2D coordinate system, such that points in each space which correspond to the same anatomical point are mapped to each other. In one embodiment, the transformation is represented, for example, by a set of non-rigid transformation parameters $(dx_T, dy_T, dz_T, r, p, w)$, where $(dx_T, dy_T, dz_T)$ represent the translations of the object, which may be a treatment target, and $(r, p, w)$ represent global rigid rotations of the target.

In one embodiment, two orthogonal x-ray projections are used to solve for these six parameters. In this embodiment, the registration in each projection is performed individually, and the results of the registration for each projection are subsequently combined, to obtain the six 3D transformation parameters. In other embodiments, however, different projections or combinations thereof may be used to solve for the transformation parameters.

FIG. 1A provides an overall schematic block diagram of a fiducial-less tracking method and system, in an embodiment of the invention in which the object being tracked is an anatomical region of a patient (e.g. a spinal region), and includes at least one treatment target and at least one reference skeletal structure. In overview, FIG. 1A shows that 2D-3D non-rigid image registration is performed for each of a pair of orthogonal projections A and B. For each projection, digitally reconstructed radiographs (DRRs) are first generated from the 3D CT scan data. As shown in FIG. 1A, the projection images A and B, acquired intra-operatively in near real time, are registered onto their respective DRRs. To determine the change in patient position and orientation between the time of the pre-operative CT scan and the time of radiosurgical treatment, local motion fields $(dx_A, dy_A)$ and $(dx_B, dy_B)$ are estimated in 2D, by using similarity measures to compare the pixel intensities in the x-ray images and the DRR images. The 3D motion field is derived from the 2D local motion fields. A full 3D motion field, derived from the local motion fields, includes 3D target translations $(dx_T, dy_T, dz_T)$ and global rigid rotations $(r, p, w)$, which are a set of non-rigid transformation parameters that represent the difference in the position and orientation of the treatment target, as shown in the projection images A and B, as compared to the position and orientation of the treatment target, as shown in the DRRs.

Figure 1B:
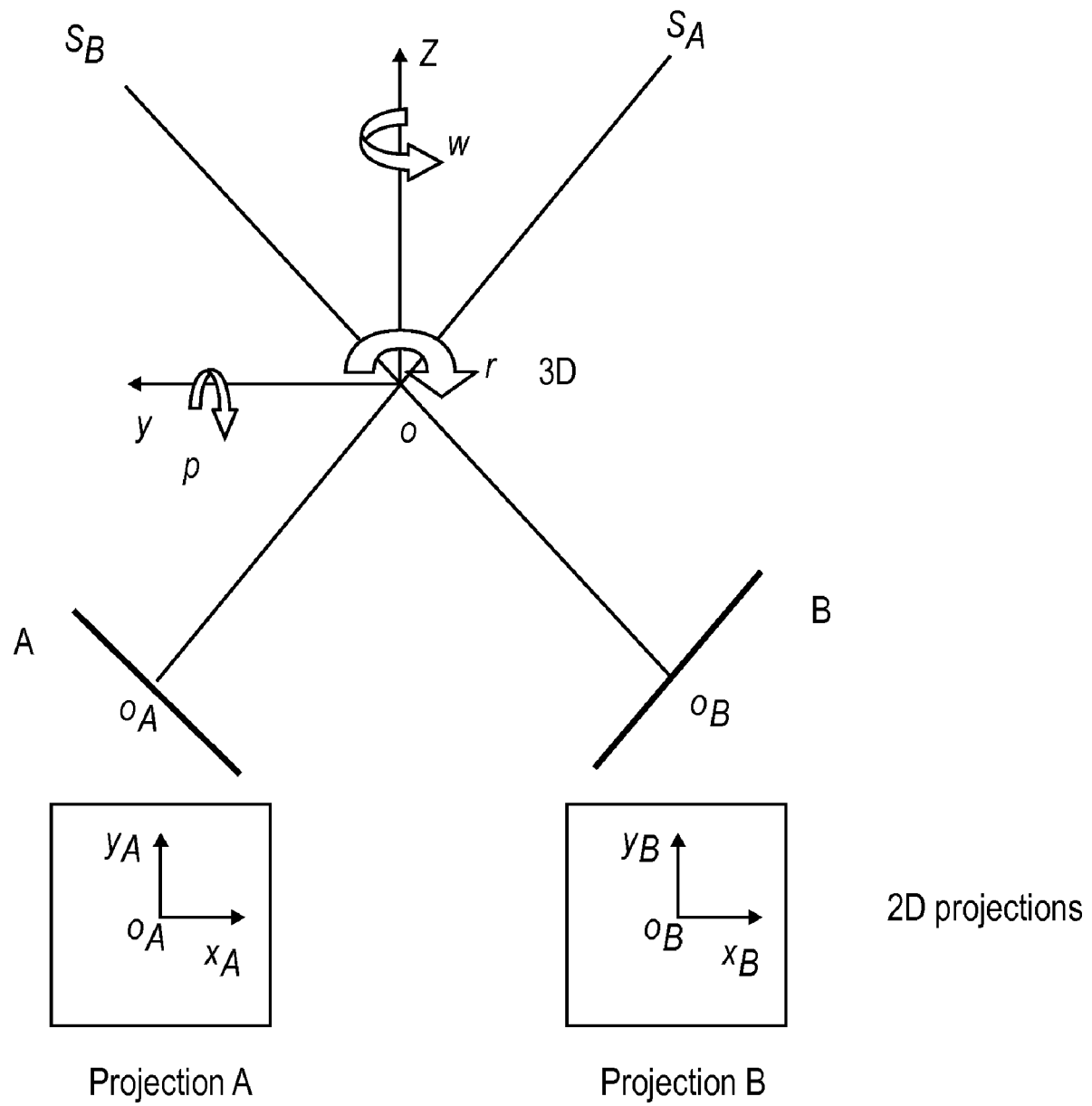
FIG. 1B illustrates the geometric relations between a three-dimensional treatment target and two orthogonal 2D x-ray projections of the target.

FIG. 1B illustrates the geometric relations between a three-dimensional treatment target, and two orthogonal 2D x-ray projections (labeled A and B in FIG. 1B), in an image registration method and system in accordance with the present invention. A pair of cameras (or image receivers) A and B receive their x-ray projections from respective x-ray sources (not shown). In the coordinate system of the 3D scan, the x-axis is directed inward into the paper, and is not indicated in FIG. 1B. As explained above, the change in position of the treatment target is represented by three translations and three global rigid rotations (dx, dy, dz, r, p, w).

In FIG. 1B, the orthogonal 2D projections A and B are viewed from the directions $o_A s_A$ and $o_B s_B$, respectively. For each of the projections A and B, FIG. 1B illustrates respective 2D planar coordinate systems that are fixed with respect to the image plane that characterizes each projection. The image planes A and B for the projections A and B are thus defined by mutually orthogonal axes within the respective coordinate systems. These axes are shown in FIG. 1B as $(x_A, y_A)$ for projection A, and $(x_B, y_B)$ for projection B. The direction of the axis $x_A$ in the 2D coordinate system for projection A, and the direction of the x-axis in the 3D scan coordinate system, are opposite with respect to each other. The direction of axis $x_B$ in the coordinate system for projection B, and the direction of the axis x in the 3D scan coordinate system, are the same.

For projection A, the 2D motion field $(dx_A, dy_A)$ is estimated by registering the x-ray image that is projected onto the image plane A, with the corresponding reference DRR image. For projection B, the 2D motion field $(dx_B, dy_B)$ is estimated by registering the x-ray image that is projected onto the image plane B, with the corresponding reference DRR image. Given the 2D motion fields $(dx_A, dy_A)$ for projection A, and $(dx_B, dy_B)$ for projection B, the 3-D target translation $(dx_T, dy_T, dz_T)$, as well as the global rigid rotations $(r, p, w)$, can be obtained for both projections A and B, by a straightforward mathematical operation.

Figure 2:
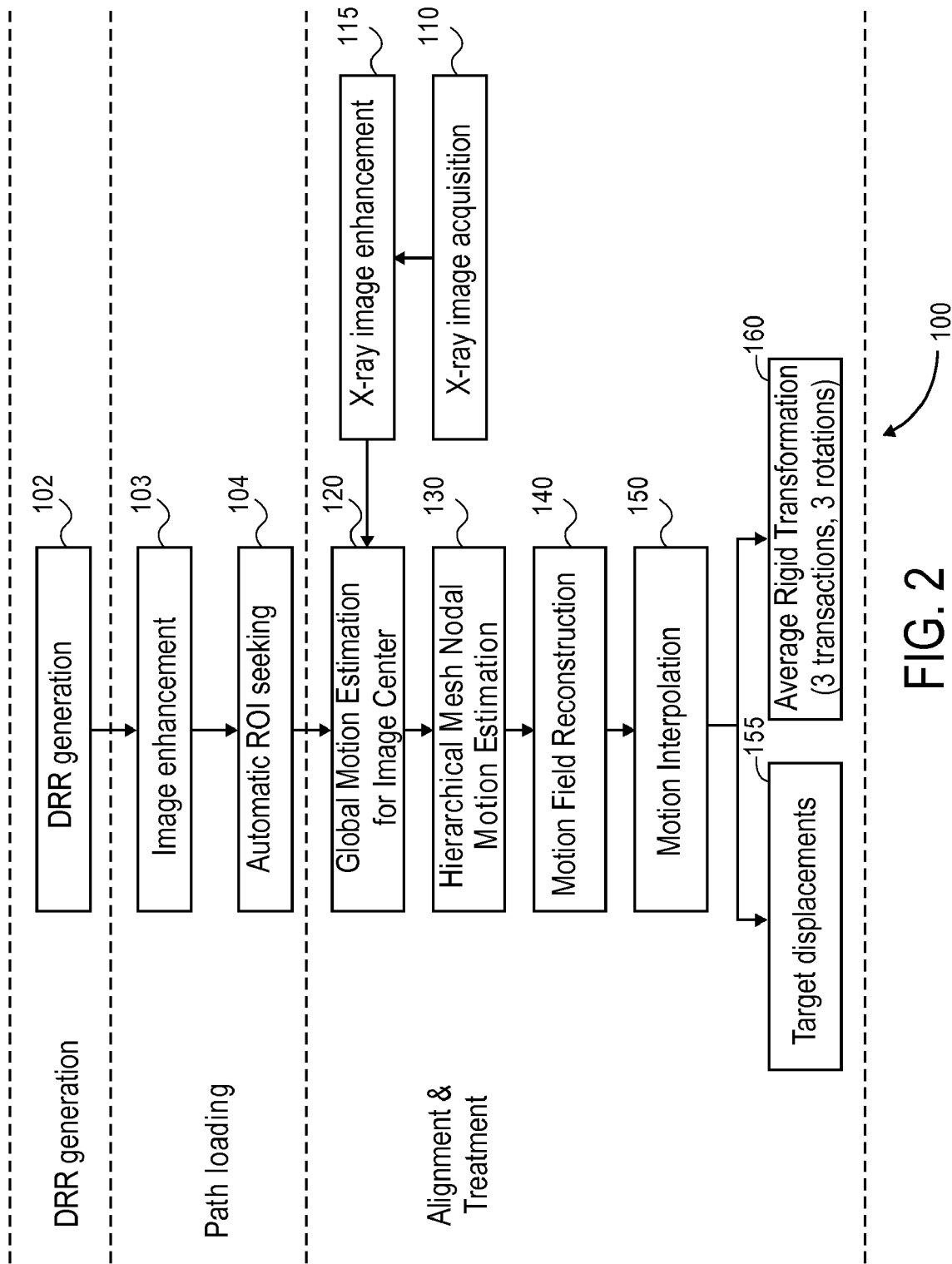
FIG. 2 illustrates a schematic flowchart of a non-rigid image registration algorithm used in one embodiment.

FIG. 2 illustrates a flowchart 100 of a non-rigid image registration algorithm. In the illustrated embodiment, the registration algorithm is used for a 2D/3D registration, performed for each projection described in FIG. 1B. In particular, non-rigid image registration is performed in the illustrated embodiment between a 2D DRR (reconstructed from pre-operative CT scan data) of a patient's target region, and an intra-operative (near real-time) x-ray projection image of the target region.

It is to be understood, however, that the method and system described in this section can be used in any other type of image registration process between a first image acquisition of an object (which may be any kind of object and is not limited to a target region within a patient), and a second image acquisition of the object. In one embodiment, the images for which non-rigid image registration is performed are discretized images each characterized by an array of pixels, each pixel having an associated pixel value representative of the intensity of the image at a surface unit area corresponding to the pixel.

As a first step, 2D DRRs (digitally reconstructed radiographs) may be generated from pre-operative 3D scan data, in step 102. An improved DRR generation process can be implemented in step 102 to bring out the skeletal structures, which are usually not easily visible in the images, or even may be hidden. In step 102, the CT scan data are modified based on a non-linear attenuation model that emphasizes the skeletal structures and thus improves the quality of the DRRs. In the image enhancement technique, implemented for the DRRs in step 103 in flowchart 100, a top-hat filter is used to bring out the skeletal structures in the DRRs generated in step 102.

In the illustrated embodiment, image registration is performed in a selected region of interest (ROI) within the enhanced DRR, in order to improve efficiency. Accordingly, an ROI is defined in the DRR, in step 104, after enhancement of the DRRs. An ROI selection process is performed that is based on image entropy, is fully automatic, and does not require user interaction. Intra-operative 2D x-ray projection images are then generated, in near real time, in step 110. Image enhancement is performed on the x-ray images, in step 115, using a top-hat filter as in step 103.

Non-rigid image registration is then performed between the enhanced x-ray images and the enhanced DRRs, within the ROI. In particular, a similarity measure is used to compare the pixel intensities in the x-ray images and the DRR images, in order to determine any change in the position and/or orientation and/or physiological deformation of the patient. In steps 120-150, a non-rigid deformation that describes real patient movement and body deformation is defined. To define the non-rigid deformation, a full motion field is constructed that is composed of many local motion fields, i.e. a plurality of locally estimated motion vectors. To estimate local motion at a given point of interest within the ROI, a similarity measure based on pattern intensity is used to compare pixel intensities.

A full motion field that is composed of many local motions can describe any desired non-rigid deformation. Further, a full motion field derived in this manner can account for non-rigid motions (translations and/or rotations) of the object, in addition to non-rigid deformations, between different image acquisitions of the object. In order to efficiently compute the local motion vectors at any point of interest within the ROI, hierarchical mesh motion estimation and multi-level block matching (performed in conjunction with an intensity-based similarity measure) are performed. These methods allow for a fast computation of the image registration algorithm 100. A smoothness constraint is imposed to reconstruct the motion field at mesh nodes in which mismatching occurred. The non-rigid transformation parameters for the non-rigid image registration are then computed from the full motion field.

In the embodiment illustrated in FIG. 2, the non-rigid deformations described by the full motion field occur in between the acquisition of the 3D CT scan data of a treatment target region in a patient, and the acquisition of the x-ray projection images of the target region. In step 120, a global translation of the entire image is first estimated. The estimated global translation is used as the initial estimate for all further local motion estimation. In the next step 130, mesh nodal motion estimation is performed, using a hierarchical mesh structure designed to estimate the local motion in multiple levels. In the next step 140, motion field reconstruction is performed for those mesh nodes in which a mismatch occurs. The reconstruction of the motion field is performed by imposing a smoothness constraint, which is based on the assumption that local motions are continuous, because of matter coherence. In step 150, the local motion vector at any desired point of interest is derived by interpolating from the nodal motions estimated for the mesh nodes that surround the point of interest. The full motion field is then constructed, using the local motion vectors derived for a plurality of desired points of interest.

In the final steps, shown as step 155 and step 160 in FIG. 2, the non-rigid transformation parameters are derived from the full motion field. In step 155, the target displacements are derived from the full motion field. In step 160, the average rigid transformation is derived from the full motion field.

Figure 3A:
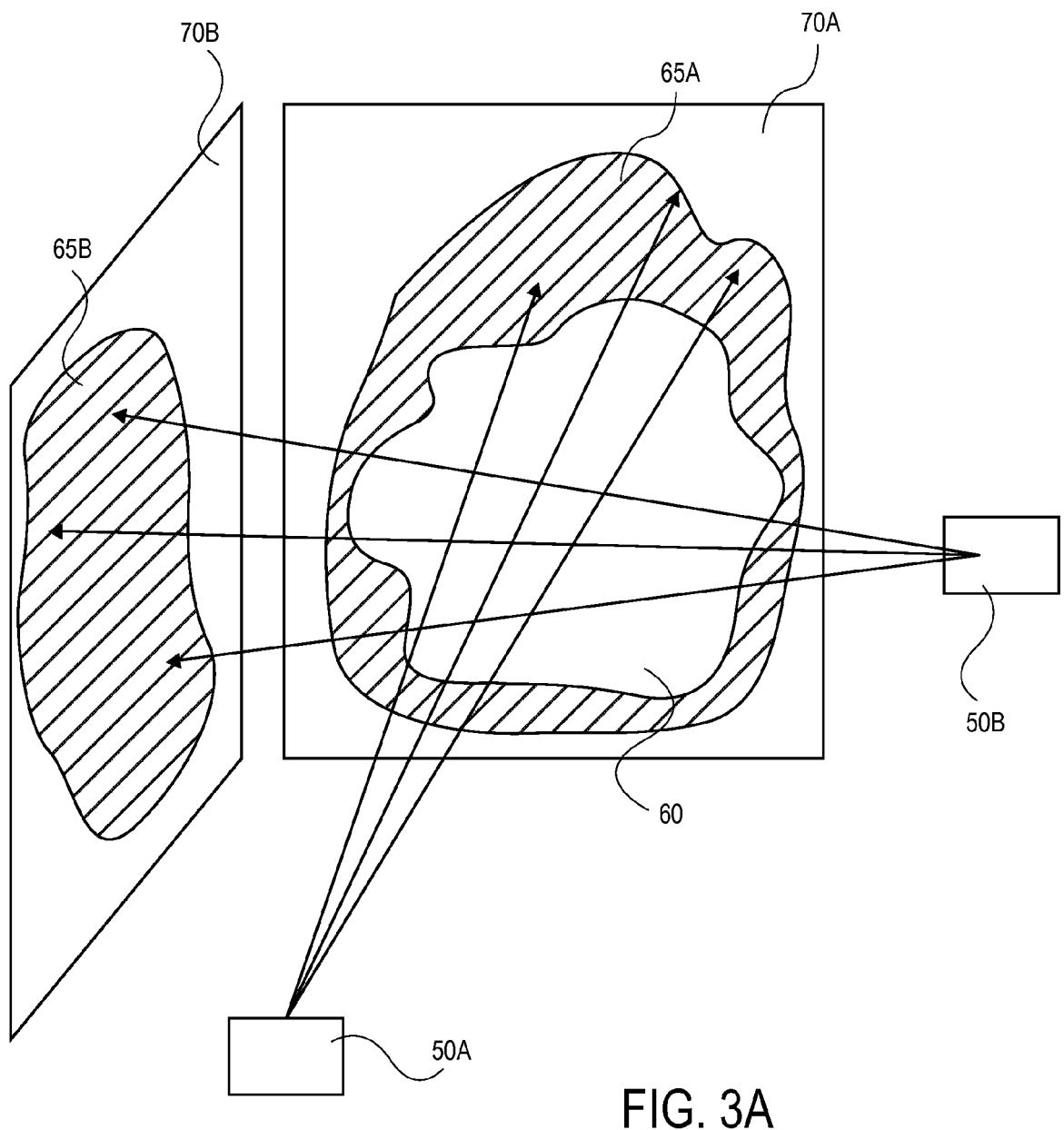
FIG. 3A schematically illustrates the generation of 2D DRRs from 3D CT scan data of an anatomical region that includes at least one treatment target and at least one reference structure.

FIG. 3A schematically illustrates the generation of 2D DRRs from 3D scan data of a treatment target within an anatomical region of a patient, as performed in step 102 in FIG. 2. In the illustrated embodiment, the 3D scan data are CT scan data; alternatively, in other embodiments other types of 3D scan data that are known, e.g. MRI (magnetic resonance imaging) scan data, PET (positron emission tomography) scan data, or ultrasound scan data, may be used. In FIG. 3A, the volumetric 3D CT image of the target is schematically referred to using reference numeral 60. The DRRs 65A and 65B, shown in FIG. 3A, are artificial, synthesized 2D images that represent the radiographic image of the target that would be obtained if imaging beams, having the same intensity, position and angle as the beams used to generate the real time x-ray projection images, were transmitted through the target, and if the target were positioned in accordance with the 3D CT scan data. The reference numerals 50A and 50B illustrate the hypothetical positions and angles from which the imaging beams would be directed through a target positioned in accordance with the CT volumetric image 60 of the target.

As known, CT scans can generate a 3D image of the target object, one axial slice at a time. Each axial CT slice can be viewed as being composed of a plurality of individual volume elements, called CT voxels. Each CT voxel is thus disposed within one of a plurality of axial voxel slices, each voxel slice representing a corresponding axial slice of the target object. Each CT voxel is characterized by a numerical value, called the CT number, which represents the x-ray attenuation characteristics of the corresponding CT voxel. A CT image of a target object can be viewed as a map or distribution within the object of a 3D array of CT numbers. The reconstruction of a CT image thus requires an accurate measurement of the x-ray attenuations, and an accurate determination of CT numbers.

Typically, DRRs are generated by casting hypothetical beams or rays through the CT volumetric image of the target. Each ray goes through a number of voxels of the 3D CT image 60. By integrating the CT numbers for these voxels along each ray, and projecting onto an imaging plane (shown as 70A and 70B, respectively, in FIG. 3A), the resultant image would emulate the radiograph that would be obtained by passing rays from hypothetical locations (50A and 50B, respectively) through a target positioned in accordance with the volumetric 3D image 60. The sum of CT numbers is performed from the source point of the hypothetical ray, onto a plane orthogonal to the central axis of the hypothetical beam. The sum is performed along each ray, an interpolated value being contributed by each voxel through which the ray passes. Each voxel contribution is interpolated over orthogonal segments along the beam path. Various known ray tracing algorithms may be used when generating DRRs.

Applications such as image-guided radiosurgery require that the comparison between the DRRs and the real-time x-ray images, as well as the subsequent adjustment of the position of the x-ray source, be made very rapidly and accurately. In practice, the accuracy should be below 1 mm, and the computation time should be on the order of a few seconds. Unfortunately, it is difficult to meet both requirements simultaneously. For example, the two different modality images, i.e. CT scan images and x-ray images, have different spatial resolution and image quality. Generally, x-ray image resolution and quality are superior to the resolution and quality of DRR images, which are only synthesized images. Typically, some structures in the DRR may appear more blurred (especially normal to the CT slice plane), compared to the x-ray image. Ideally, an optimal similarity measure for a 2D/3D registration process should allow for an accurate registration to be achieved, despite such differences. Also, DRR generation relies on a proper attenuation model. Because attenuation is proportional to the mass intensity of the target volume through which the beam passes, the exact relationship between the traversed mass intensity and the CT image intensity needs to be known, in order to obtain an accurate modeling. Establishing this relationship is difficult, however, so the linear attenuation model is often used, in conventional methods and systems for DRR generation.

As is known, the linear attenuation coefficient of a material is dependent on x-ray energy. CT machines and x-ray machines work at different effective energies, however. As a result, the attenuation coefficients measured by a CT scanner are different from the attenuation of a beam of x-rays passing through the target. The skeletal structures in DRR images cannot be reconstructed very well using the linear model, the DRRs being only synthetic x-ray projection images. At the CT scan x-ray energies, the ratio of bone-to-soft-tissue attenuation is much lower than at the x-ray radiographic projection energies. Thus, in a DRR produced from a 3D CT volume, the image contrast from soft tissue tends to be comparable with the image contrast from bone, reducing the clarity of bone details, for example.

The quality of DRR images relies on proper attenuation modeling, as well as a proper interpolation scheme for interpolation the CT numbers. In one embodiment, an improved DRR generation is accomplished during step 102 (as shown in FIG. 2), by formulating an improved x-ray attenuation model for fiducial-less tracking, so that the DRRs become more like the real x-ray projection images. A linear attenuation model is no longer assumed, and the CT numbers are modified in order to compensate for the above-mentioned a difference in the bone-to-tissue attenuation ratio. On the basis of many experiments conducted with patient clinical data, the following empirical equation was formulated to modify the original CT numbers:

$$C(x,y,z) = aC_0(x,y,z)e^{bC0(x,y,z)} \quad (1)$$

where $C(x,y,z)$ represents the modified CT number of a 3D CT voxel located at a point $(x,y,z)$;

a and b represent weighting coefficients;

and $C_0(x,y,z)$ represents the unmodified CT number, based on a linear attenuation model, of a 3D CT voxel having a location $(x,y,z)$.

Figure 3B:
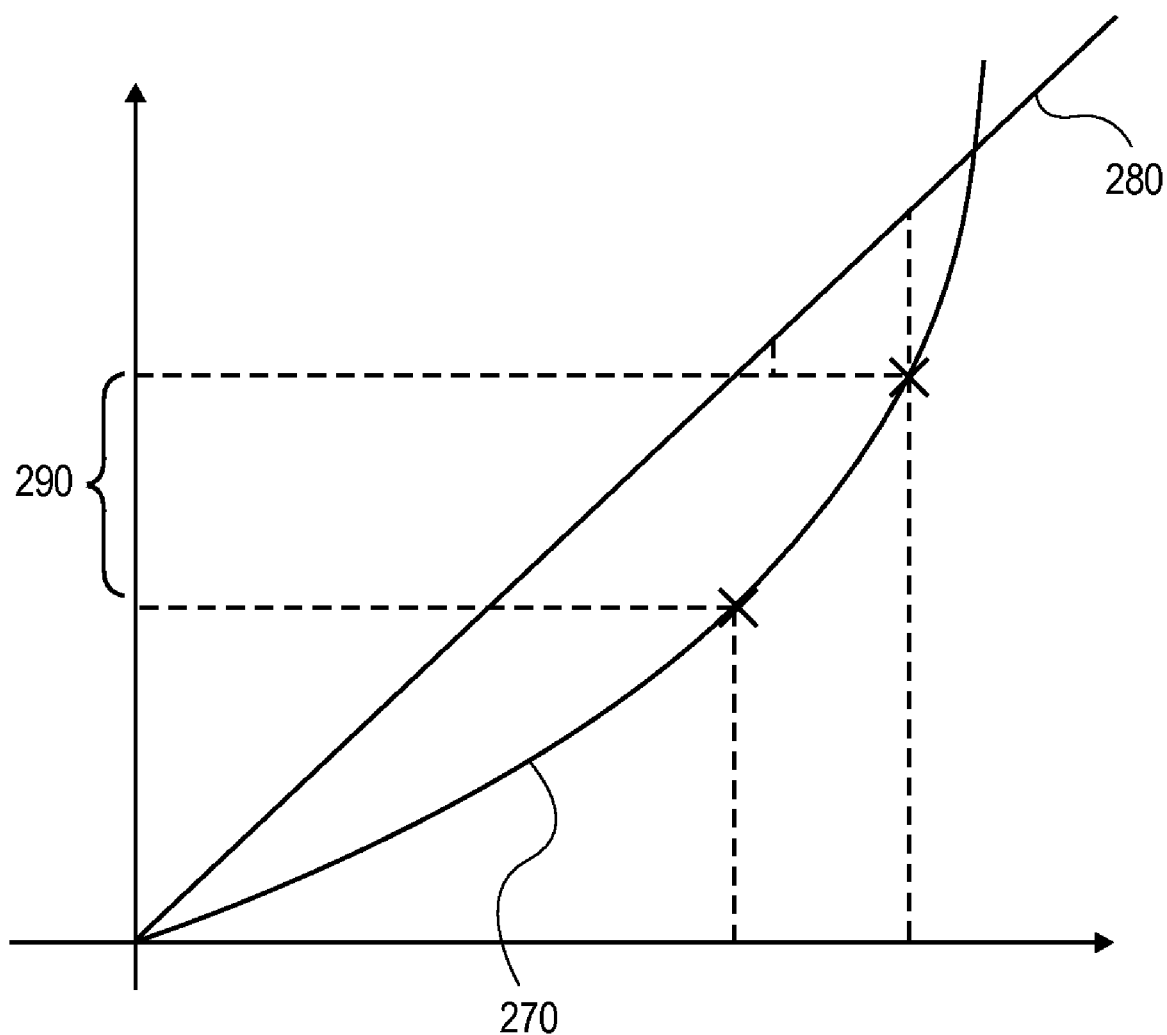
FIG. 3B is a schematic plot of a non-linear x-ray attenuation model for modifying CT numbers, in order to generate improved quality DRRs.

FIG. 3B provides a schematic plot of equation (1). In FIG. 3B, the curve identified by reference numeral 270 represents CT numbers resulting from the non-linear attenuation model provided by the empirical formula (1), whereas the curve identified by reference numeral 280 represents CT numbers resulting from a linear attenuation model. After modification of the CT numbers using equation (1), skeletal structures in the images are emphasized, and soft tissues are suppressed. In other words, use of the empirical formula (1) to process CT numbers during DRR generation serves to bring out the skeletal features against the tissue background, in the DRRs. In the region identified in FIG. 3B with reference numeral 290, the details of the rigid structures (e.g. skeletal structures) are more easily visible using the non-linear attenuation curve 290, since the details are spread over a broader range of intensity values, as compared to the linear attenuation curve 280. Empirically, the weighting coefficient b in equation (1) is 128 for 8-bit images, whereas the weighting coefficient a is slightly different for the cervical, thoracic and lumbar cases, respectively.

The interpolation scheme used in one embodiment to improve the quality of DRRs is bi-linear interpolation. In this embodiment, bi-linear interpolation is performed in step 210, to integrate the CT numbers along the CT voxels that are encountered by each cast ray. In one embodiment, the bi-linear interpolation is followed by a 1-D polynomial interpolation over three voxel slices, for each voxel of interest. The three voxel slices include the voxel slice containing the voxel of interest, plus each adjacent voxel slice.

Fiducial-less tracking relies on skeletal reference structures that are usually not easily visible, or may even be hidden in the DRRs and in the x-ray projection images. Because fiducial-less tracking is based on registration of such skeletal structures, both the DRR and the x-ray images have to be enhanced to bring out the details of the vertebral structures and improve their visibility. In one embodiment, therefore, image enhancement is undertaken for both the DRRs and the x-ray projection images. In most thoracic and lumbar cases, the skeletal structures are not easily visible or even hidden in DRR and X-ray images. For these cases therefore, enhancement of the DRR and the x-ray images is necessary, in order to make registration at all possible. In cervical cases, the skeletal structures of spine are well visible in both the DRR and the x-ray images, but the details of the structures are still not clear. Accordingly, in cervical cases, the DRR and the x-ray images should be enhanced to improve the registration.

Figure 4:
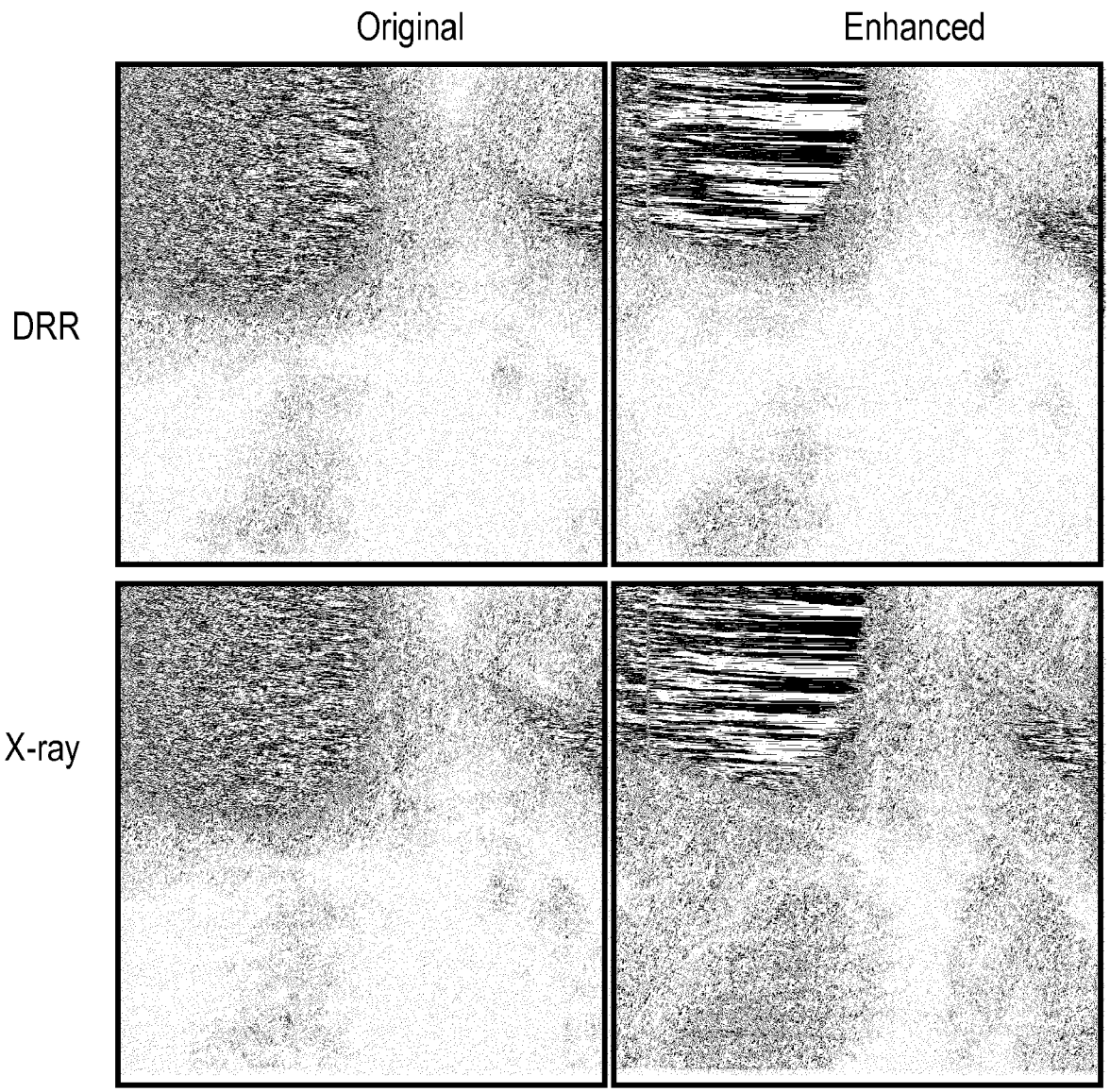
FIG. 4 illustrates exemplary images that have been enhanced to increase the visibility of skeletal structures, using top hat filtering.

FIG. 4 illustrates exemplary images that have been enhanced to increase the visibility of skeletal structures, using top hat filtering. In the embodiment illustrated in FIG. 4, a top-hat filter was designed and used to enhance the x-ray images (step 115 in FIG. 2) and to enhance the DRR images (step 103 in FIG. 2). In particular, the skeletal structures in the images have been enhanced, i.e., brought out, by applying a top hat filter operator to the pixels of the x-ray projection images and the DRR images. As known, a top hat filter is a nonlinear operator that finds the brightest pixels in two different size neighborhoods, then keeps the extreme values. In one embodiment, the top hat filter operates as follows: if the brightest value in the smaller neighborhood region is greater that the value in the larger neighborhood, by an amount determined by a user-entered threshold, then the pixel remains, otherwise it is eliminated. As a result of applying a top hat filter to the images, it is possible to locate features of interest.

In one embodiment, the top-hat filter is designed by using a weighted combination of image opening and closing with a certain structural element. The top hat filter operator is defined mathematically as follows:

$$f_e = f + w \times [f - \gamma_B(f)] - b \times [\varphi_B(f) - f] \quad (2)$$
$$= f + w \times WTH(f) - b \times BTH(f)$$

where $f_e$ represents the enhanced image, resulting from the application of the top hat filter operator to each pixel in the original image;

f represents the original image;

w and b represent weighting coefficients, $\gamma_B(f)$ represents a structural element for the opening of the original image f, and $\phi_B(f)$ represents a structural element for the closing of the original image f.

In expression (2) above, $WTH(f) = f - \gamma_B(f)$ is called a white top-hat filter, whereas $BTH(f) = \phi_B(f) - f$ is called a black top-hat filter. The structural elements $\gamma_B(f)$ and $\phi_B(f)$ are masks that are used to perform the basic morphological operation. The sizes of the structural elements vary slightly for cervical, thoracic, and lumbar applications. The empirical values are determined experimentally. The weighting coefficients w and b are determined adaptively by the amplitudes of WTH(f) and BTH(f), respectively. Empirically, the values of the weighting coefficients w and b have been found to be about 1 each (w=1, b=1), for a cervical case in which less tissue is present. In the lumbar case, in which more tissue is present, the values of w and b have been found to be greater than about 2 each (w>2, b>2). In the lumbar case, the weighting process brings out the skeletal structures to a greater degree, compared with the cervical case.

In one embodiment, image registration is conducted only in a certain region of interest (ROI) defined in the DRR. The ROI contains the treatment target (e.g. a tumor or lesion). In one embodiment, image entropy is specifically defined, in step 104 in FIG. 2. In this way, the ROI can be automatically selected, for optimum registration, minimizing or even eliminating user interaction. Because image registration relies on the image content or image information, in this embodiment the ROI is optimized to contain as much information as possible.

The Shannon entropy, known from conventional communication theory, is commonly used as a measure of information in signal and image processing. It is defined as $H = -\Sigma_i^n p_i \log p_i$, where H represents the average information supplied by a set of n symbols whose probabilities are given by $p_1, p_2, \ldots, p_n$. When applied to the pixels of each image (as enhanced in steps 103 or 115 in FIG. 2), the Shannon entropy for each image is defined by: $H = -\Sigma_I p(I) \log p(I)$, where I is the image intensity level, and p(I) is the probability of an image intensity value I occurring within the ROI. In the original formulation by Shannon, any change in the data that tends to equalize the probabilities $p_1, p_2, \ldots, p_n$ increases the entropy, as observed by Shannon. For a given image, the Shannon entropy is conventionally calculated from a image intensity histogram, in which the probabilities $p_1, p_2, \ldots, p_n$ are histogram entries.

In one embodiment, the Shannon entropy H is modified, based on the fact that the skeletal structures occur in bright areas. In this embodiment, a modified Shannon entropy is used for each image, which is defined as follows:

$$H = -\Sigma_I I p(I) \log p(I), \quad (3)$$

where again I is the image intensity level, and p(I) is the probability of the image intensity value I occurring within the ROI. In step 104 (shown in FIG. 2), the modified Shannon entropy is first determined for the enhanced DRR image. Once the modified Shannon entropy H is calculated, an ROI is then automatically selected by determining the region within the DRR for which the entropy H is maximized. Subsequent steps in the image registration process (steps 120-150 in FIG. 2) take place only within the ROI.

Restricting the image registration process to within a ROI has several advantages. One advantage is that such a restriction can speed up the registration process, since the registration needs to be performed only for the ROI. For example, the similarity measure needs only be computed for the ROI, and block matching need only be performed within the ROI. Further, the registration process is more accurate when limited to an area within the ROI. The more limited region in which registration is conducted, the less likely it is that structures within the ROI would have moved relative to each other between the time of the pre-operative CT scans and the time of the medical treatment.

Based on the improved and enhanced DRRs (step 103 in FIG. 2), and the enhanced x-ray projection images (step 115 in FIG. 2), in which the skeletal reference structures have been brought out to make fiducial-less tracking possible, a non-rigid deformation of the anatomical region is determined in steps 120-150 (shown in FIG. 2). In this patent, a 'rigid body' assumption, i.e. which is often made in image registration applications, and which assumes that between image acquisitions, the anatomical and pathological structures of interest do not deform or distort, is not made. There is no longer a need to preserve the 'rigid body' constraints, i.e. to require that the body be rigid and not undergo any local variations during the transformation. Based on an abundance of observations and analyses on clinical patient data, in the present patent a non-rigid deformation is assumed, in lieu of a rigid transformation, to obtain an improved description of the real patient movement and body deformation. By computing a non-rigid deformation field, patient position/orientation can be more reliably monitored corrected during the initial alignment, as well as throughout the entire treatment.

A non-rigid image registration allows the inherent local anatomical variations that exist between different image acquisitions to be accounted for, in contrast to a rigid image registration which does not allow the overcoming of such variations. Non-rigid registration defines a deformation field that provides a translation or mapping for every pixel in the image. In one embodiment, a full motion field, composed of many local motion vectors or fields, is computed in order to derive the non-rigid deformation field.

In order to estimate local motion fields, in one embodiment, a multi-level block matching method is used in conjunction with a similarity measure based on pattern intensity. This approach allows the local motion to be rapidly and accurately estimated in most parts of the ROI. Multi-level block matching, which allows for computational efficiency, is described in conjunction with a rigid registration algorithm, in a commonly owned application, U.S. Ser. No. 10/652,786 (the "'786 application"), incorporated by reference in its entirety. A similarity measure based on pattern intensity, used in conjunction with a registration algorithm based on rigid transformations, i.e. the "FAST 6D algorithm" developed by Accuray, Inc. for use with the Cyberknife radiosurgery system, is described in full in commonly owned applications, U.S. Ser. Nos. 10/652,786 (the "'786 application"), 10/652, 717 (the "'717 application"), and 10/652,785 (the "'785 application"), which are all incorporated by reference in their entireties. In the present patent, the pattern intensity based similarity measure and the multi-level block matching method are used in conjunction with a registration algorithm based on a non-rigid (rather than a rigid) transformation. The pattern intensity-based similarity measure, originally developed for a rigid image registration algorithm, provides a powerful and efficient technique for solving the 2D/3D image registration problem, also in a non-rigid framework.

In one embodiment, block matching is performed, i.e. a small block centered around a point of interest is used in order to locally estimate the displacements at each desired point within the ROI. As known, when using block matching to register a first image onto a second image, the first image is divided into different blocks, typically rectangular boxes of equal size. Each point of interest, which may be a mesh node, or may be a non-node pixel that is surrounded by mesh nodes, is taken as the center of one of the blocks. These blocks are then translated so as to maximize a local similarity criterion, which in one embodiment is the pattern intensity based similarity measure, described above.

In block matching methods, it is generally assumed that each pixel in a block has the same motion, and a block matching algorithm is typically used to estimate the motion vectors for each block. In a block matching algorithm used in one embodiment, a search is conducted for a matching block in the second image, in a manner so as to maximize a measure of similarity, based on pattern intensity, between the respective blocks. The search is for a location of the maximum in the similarity measure function, the maximum representing the existence of a matching block in the second image. The search may be conducted within a search window that is defined around the point of interest and that contains the block.

In any block matching algorithm, it is important to optimize the search strategy, and to select an appropriate block size. For small blocks, the translational rigid model is typically assumed. Even though rigid rotations or some other complicated deformations exist, the rigid body translation model is valid for estimating the translations for the block center point. When rotations or other deformations exist in addition to the translations, the accuracy increases with decreasing block size, and decreases with increasing block size. With the use of smaller block sizes, however, the possibility of mismatching increases. In one embodiment, a block size selection strategy is adopted in which it is assumed that larger blocks are needed for larger displacements, and that smaller blocks are need for smaller displacements.

Figure 5A:
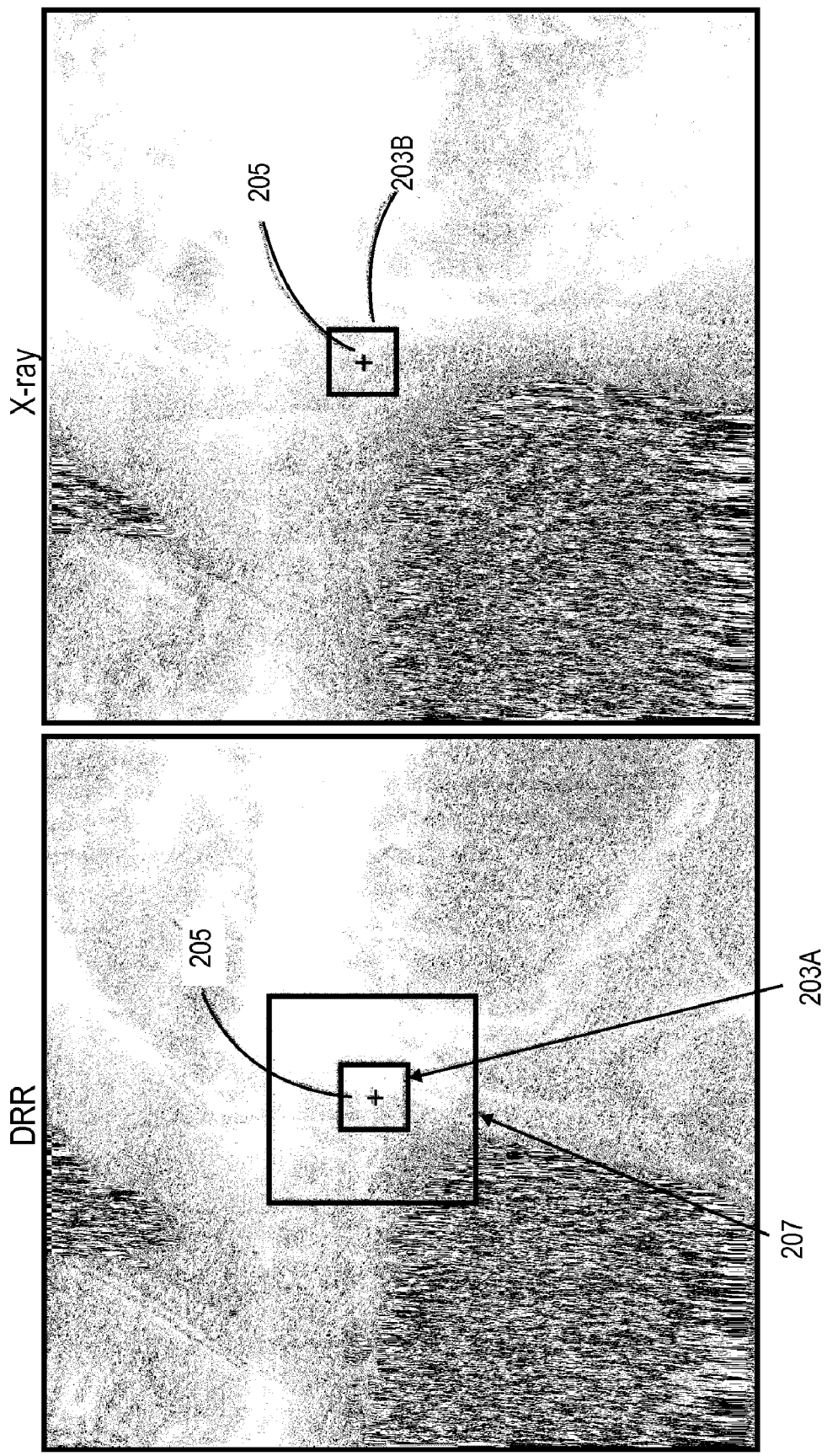
FIGS. 5A and 5B schematically illustrate local motion estimation for a given point of interest within a target in a patient, using block matching.
Figure 5B:
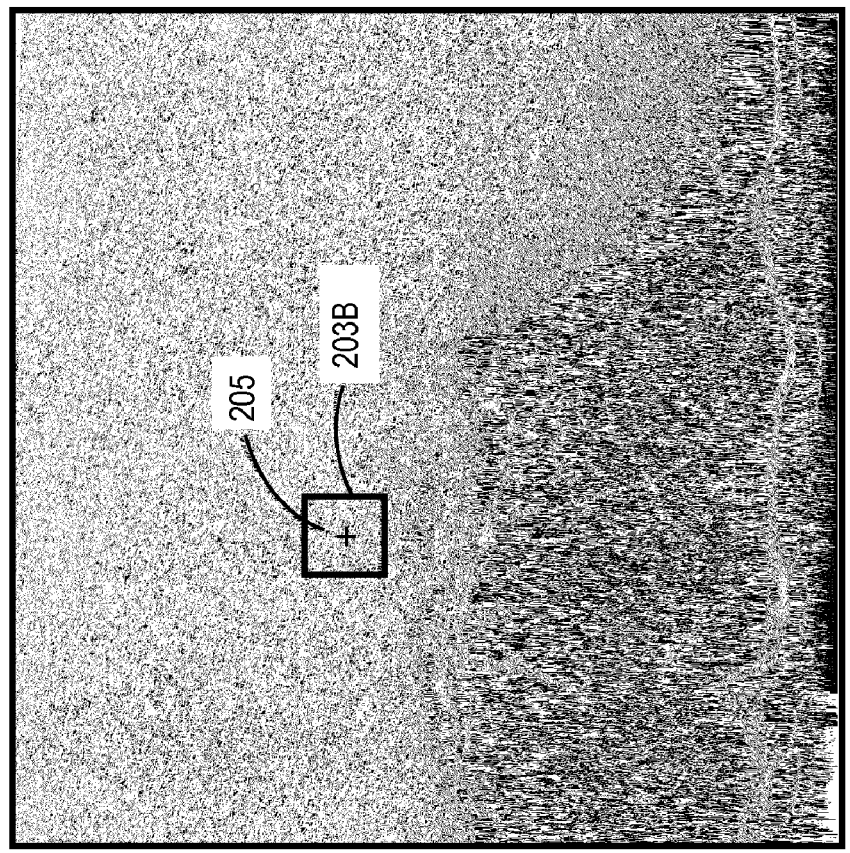
Figure 5B:
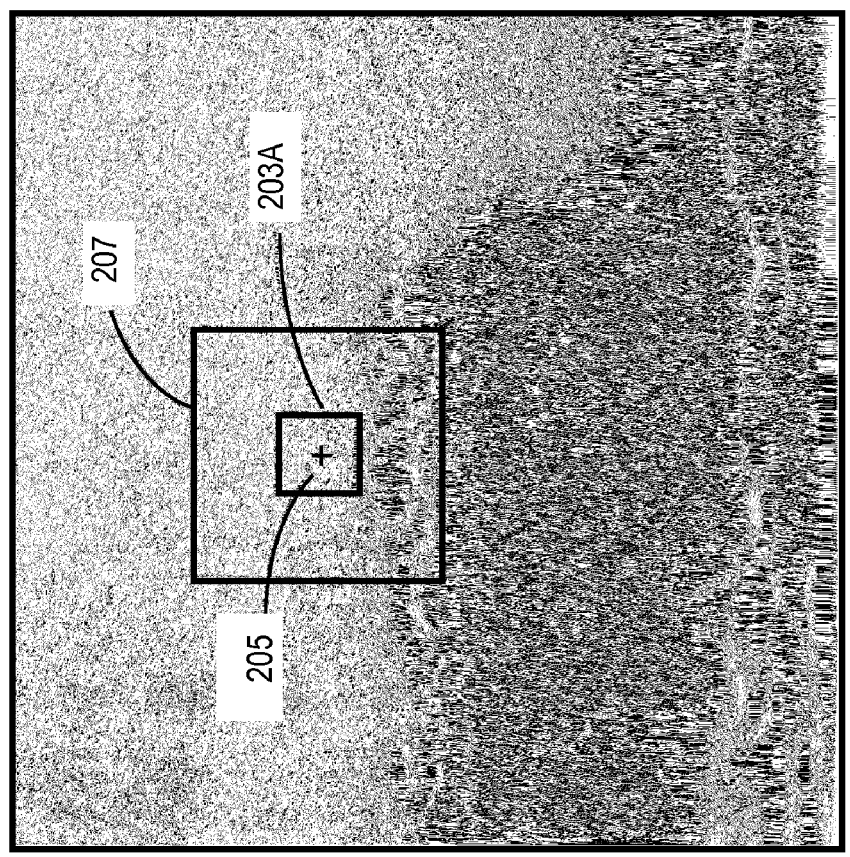

FIGS. 5A and 5B schematically illustrate local motion estimation for a point of interest within a target in a patient, using block matching. In the embodiment illustrated in FIG. 5A, the target is located in the cervical region of the spine, whereas in the embodiment illustrated in FIG. 5B, the target is located in the thoracic region. In both FIGS. 5A and 5B, the left and the right pictures are the DRR and X-ray images, respectively. In each figure, a small block 203A is defined around a point of interest 205 in the DRR. Also, a search window 207 that encompasses the block 203 is defined in the DRR. The matching block in the x-ray image is indicated in the figures with reference numeral 203B. In the embodiment illustrated in FIGS. 5A and 5B, the size of the search window 207 is 48 mm×48 mm, and the block size is 15×15 mm. It can be seen, simply by visual inspection, that the point of interest 205 is well located in the X-ray image.

Figure 6:
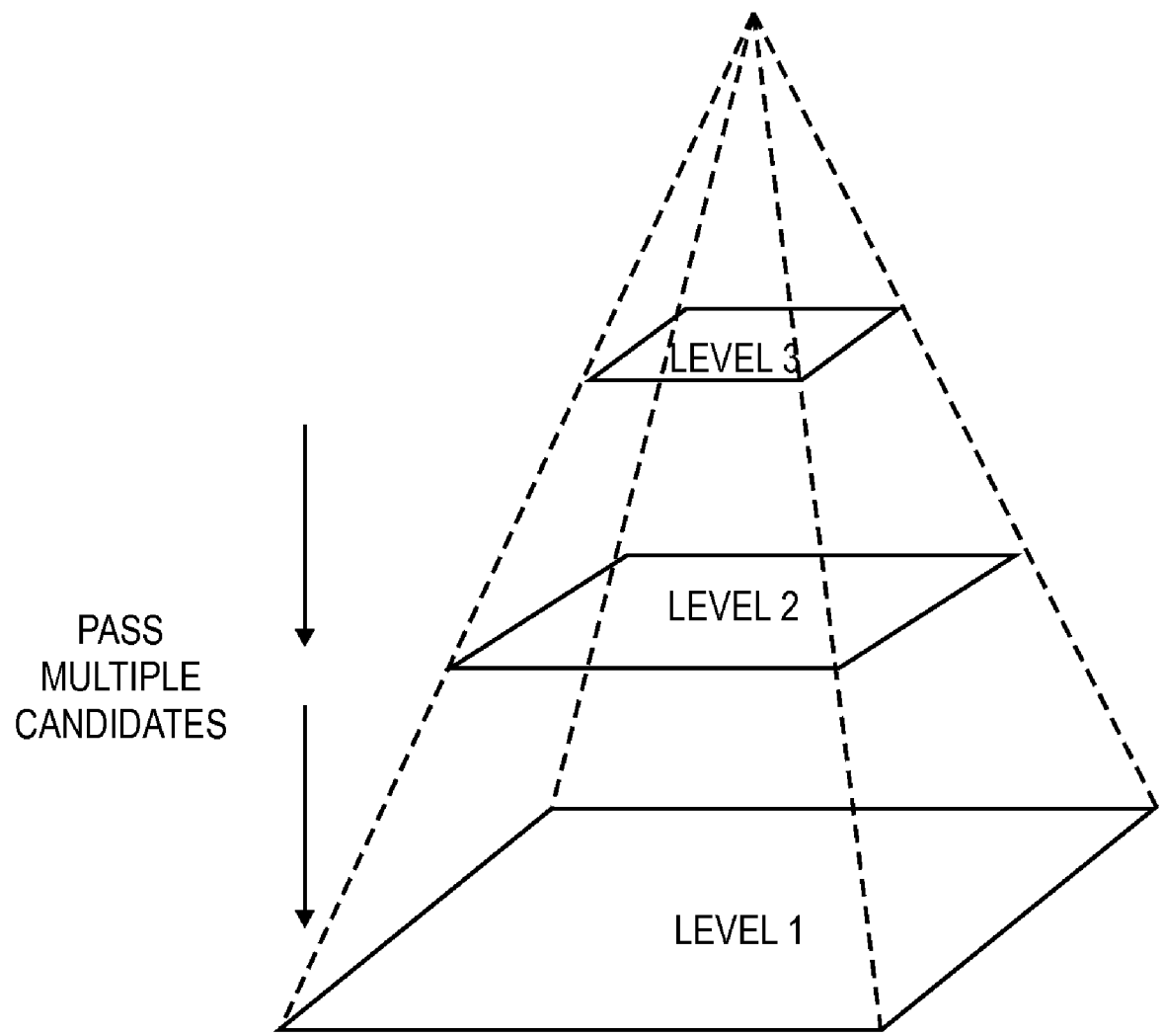
FIG. 6 schematically illustrates multi-level block matching, in one embodiment.

FIG. 6 schematically illustrates a multi-resolution image representation, when implementing multi-level block matching, using multiple candidates. Multi-level block matching is a fast search method that uses the displacement estimates made at a lower level as the initial results for subsequent search phases. The basic idea in multi-level block matching is to match the images at each of a plurality of resolution levels, successively, starting from the lowest resolution level and moving up to the highest resolution level. The full-size image, having the highest resolution level, is shown at the bottom in FIG. 6, as level 1. The upper images (level 2 and level 3) have successively lower spatial resolutions, the image having the lowest resolution being shown as level 3. The lower resolution images are obtained by lower pass filtering, and sub-sampling the full-size images.

In FIG. 6, assuming that the full image block size is W×H in Level 1, the block sizes are $$\frac{W}{2} \times \frac{H}{2} \text{ and } \frac{W}{4} \times \frac{H}{4}$$

in Level 2 and Level 3, respectively, as indicated in the figure. In the lowest resolution level (Level 3), a large search range is used to enable estimation of large displacements. A very small search range (−2, +2) is used in the rest of the resolution levels.

The results at the lower resolution level serve to determine rough estimates of the displacements. The output at the lower level is then passed onto the subsequent higher resolution level. The estimated motion vector (in most cases, a translation vector) for the block is successively refined, using the higher resolution images. In the final matching results, the accuracy of the estimated translations depends on the spatial resolution of the highest resolution images (shown as level 1 in FIG. 6).

There is some risk in multi-level matching. It is possible that the estimate at lower levels may fall in a local maximum, and far away from the global maximum that is being sought. In this case, further matchings at subsequent higher resolution levels may not converge to its global maximum. To overcome this risk, multiple candidates are used for the estimates, in one embodiment. Many candidates that have shown optimal matching results are passed on from the lower levels to the higher resolution levels. The more candidates that are used, the more reliable are the estimates. In one embodiment, the best candidates are ranked by the similarity measure function values.

In one embodiment, a similarity measure based on pattern intensity is used, in conjunction with multi-level block matching. As mentioned earlier, this similarity measure is a key element contributing to the success of the "FAST 6D algorithm," described in the commonly owned '786 application, '717 application, and '785 application. In one embodiment, the similarity measure is determined by forming a difference image between the "live" (or near real time) x-ray projection images and the DRR images, and applying upon each pixel of the difference image a pattern intensity function. Specifically, the difference image $I_{dif}(i,j)$ is formed by subtracting a corresponding pixel value of the pre-operative DRR image from each pixel value of the intra-operative x-ray projection image, within the ROI:

$$I_{dif}(i,j) = I_{Live}(i,j) - I_{DRR}(i,j) \quad (4)$$

In equation (4), I(i,j) represents the image intensity value of a pixel located at the i-th row and j-th column of each pixel array for the respective image. Specifically, $I_{dif}(i, j)$ represents an array of pixel values for a difference image formed by subtracting the corresponding pixel values of the second image from each pixel value of the first image. $I_{live}(i,j)$ represents the (i,j)-th pixel value of the first image of the object. $I_{DRR}(i,j)$ represents the (i,j)-th pixel value of the second image of the object. The similarity measure operates on this difference image, and is expressed as the summation of asymptotic functions of the gradients of the difference image over the pixels within a neighborhood R:

$$\sum_{i,j} \sum_{k,l \subset R} \frac{\sigma^2}{\sigma^2 + (I_{dif}(i, j) - I_{dif}(i+k, j+l))^2} \quad (5)$$

In equation (5) above, the constant σ is a weighting coefficient for the pattern intensity function. The sensitivity of the solution to the variation of x-ray image can be minimized by careful selection of this constant. The larger the weighting coefficient, the more stable the results. However, the choice of a entails a tradeoff between stability and accuracy. When the value of σ is too large, some small details in the images cannot be reflected in the similarity measure. Based on the experiments, the empirical value for σ is in the range from about 4 to about 16, in one embodiment.

Figure 7:
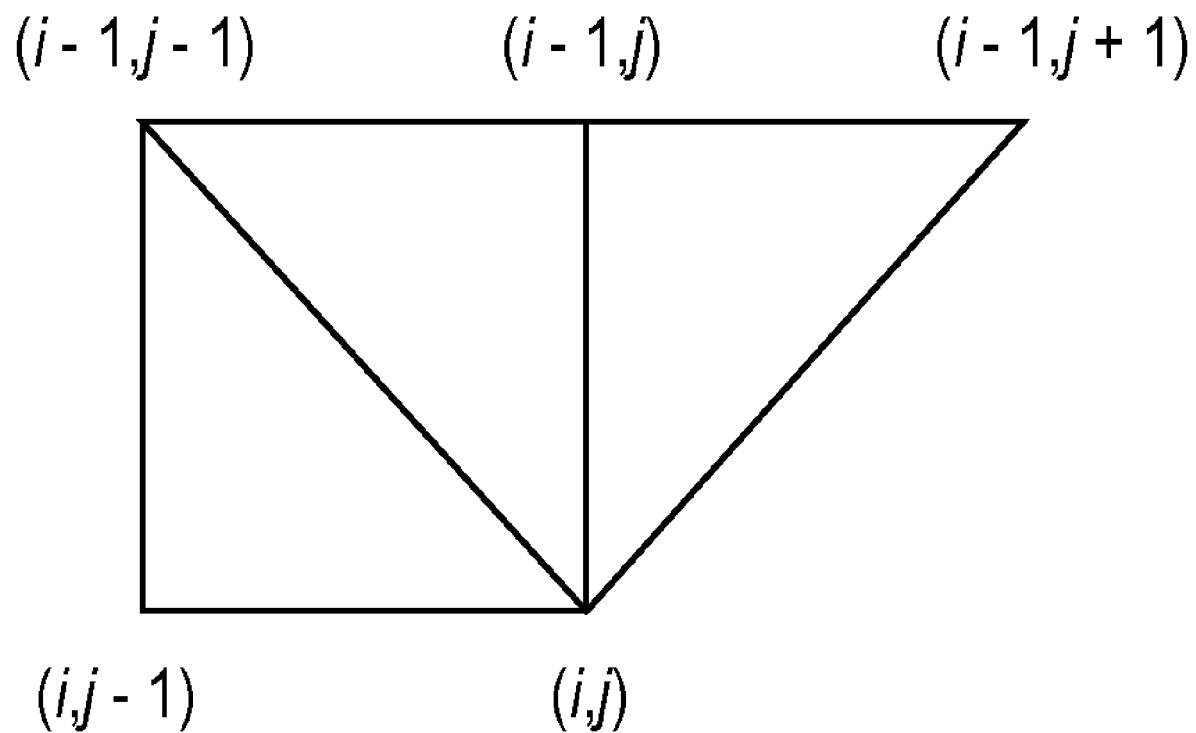
FIG. 7 schematically illustrates a neighborhood R for calculating a similarity measure based on pattern intensity.

FIG. 7 schematically illustrates a neighborhood R for calculating a similarity measure based on pattern intensity. As seen from FIG. 7, the neighborhood R in the illustrated embodiment is defined so that the gradients of the difference image can be considered in at least four directions (horizontal, vertical, 45° diagonal and −45° diagonal). When the neighborhood R is defined in this manner, equation (5) for the similarity measure becomes:

$$\sum_{i,j} \frac{\sigma^2}{\sigma^2 + ((I_{diff}(i,j) - I_{diff}(i,j-1))^2} + \qquad (6)$$

$$\sum_{i,j} \frac{\sigma^2}{\sigma^2 + ((I_{diff}(i,j) - I_{diff}(i-1,j))^2} +$$

$$\sum_{i,j} \frac{\sigma^2}{\sigma^2 + ((I_{diff}(i,j) - I_{diff}(i-1,j-1))^2} +$$

$$\sum_{i,j} \frac{\sigma^2}{\sigma^2 + ((I_{diff}(i,j) - I_{diff}(i-1,j+1))^2}.$$

Equations (5) and (6) for pattern intensity have several advantages. First, the difference image filters out the low frequency part that predominantly consists of the soft tissues, and keeps the high frequency part that predominantly consists of the skeletal structures. This feature makes the algorithm robust to some brightness intensity difference between live and DRR images. Second, because of the asymptotic function, the measure is less affected by the pixels whose intensity value slightly deviates from its neighboring pixels. These types of pixels are thought to contain random noise. Third, because the asymptotic function quickly approaches to zero when the variable increases, large intensity differences such as image artifacts have the same effects on the similarity measure regardless of their magnitude. Due to this feature, the pattern intensity is less sensitive to image artifacts.

Figure 8A:
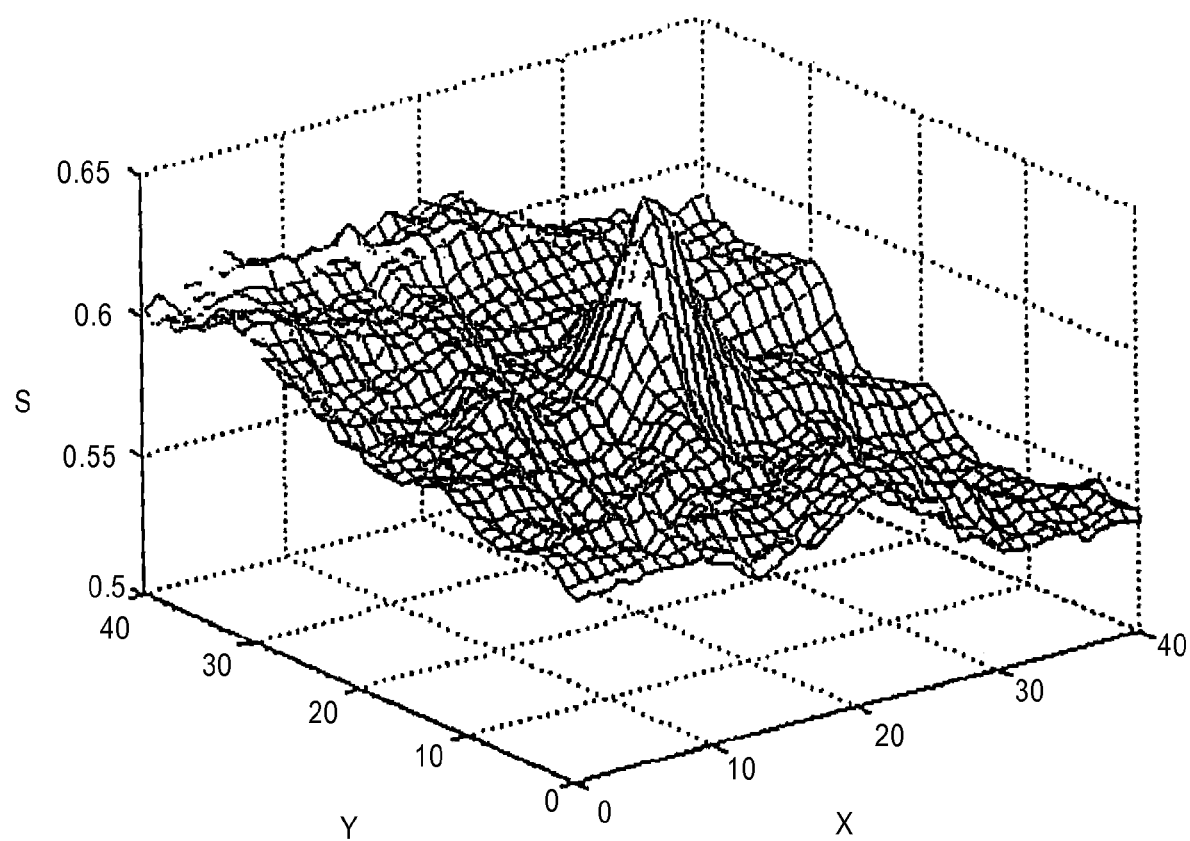
FIGS. 8A and 8B provide plots of the similarity measure functions used for the local motion estimation illustrated in FIGS. 5A and 5B, respectively.
Figure 8B:
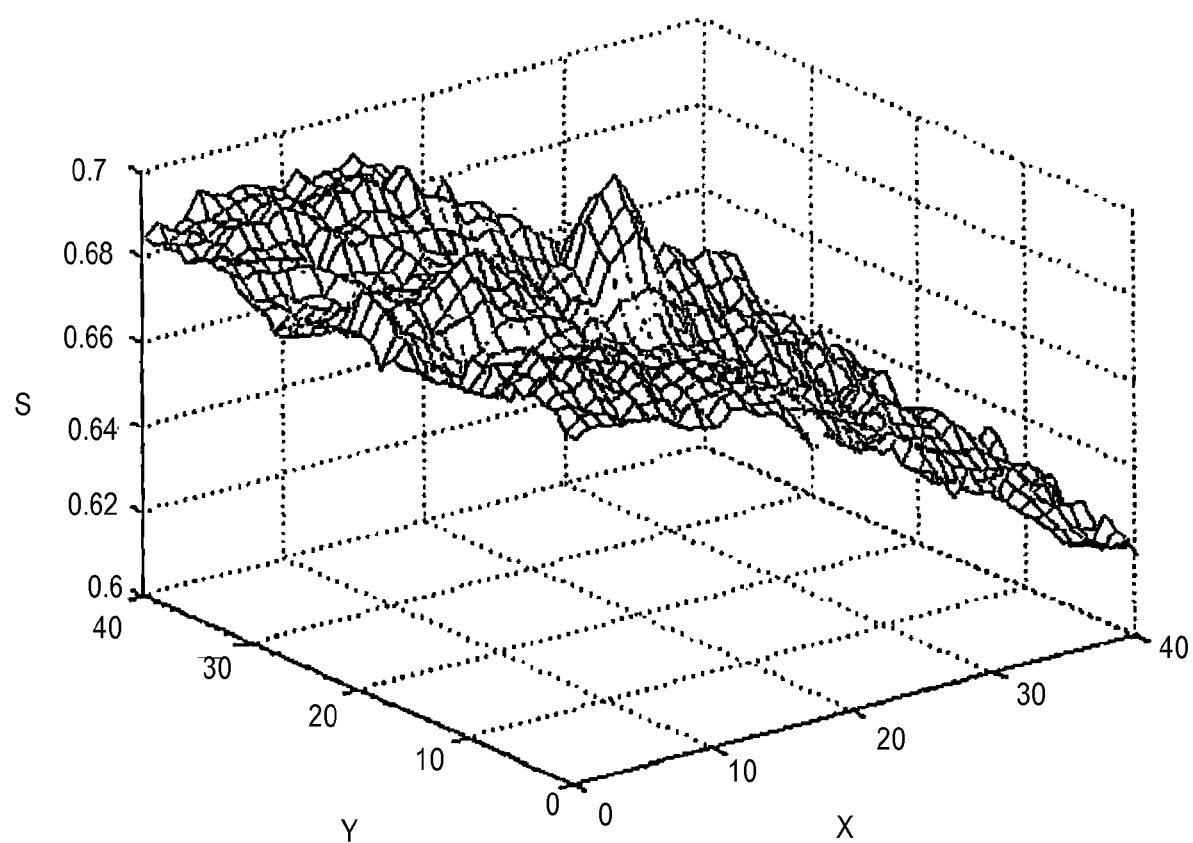

FIGS. 8A-8B provides a plot of the similarity measure function that was used for the local motion estimation illustrated in FIGS. 5A-5B, and that is based on equations (5) and (6). The similarity measure function is plotted with respect to translations in two mutually orthogonal directions (x- and y-). The existence of the global maximum is clearly shown, in both FIG. 8A and FIG. 8B. Several local maximum points also exist in FIGS. 8A and 8B, however. This indicates that the use of multiple candidates may be necessary in multi-level block matching, as explained above.

The estimation of local motion fields using block matching together with hierarchical mesh motion estimation, as well as the reconstruction of the full motion field from the plurality of locally estimated motion fields, are performed in steps 120-150 of the flowchart shown in FIG. 2. Fast generation of the full motion field is achieved by using hierarchical mesh tracking, and using SIMD (single instruction multiple data) technology to perform image computation in parallel.

In one embodiment, a global translation of the entire image (measured as a translation of the image center of the image) is first estimated, then used as the initial estimates for all further local motion estimation. In other words, a rough estimate is made of the center displacement for the entire image, and is used as the starting estimate for all local displacements. Referring back to FIG. 2, the first step (indicated with reference numeral 120 in FIG. 2) in generating a full motion field for a target, between the pre-operative scan and the intra-operative treatment, is the step of estimating a global translation for the entire image, or equivalently, estimating the center displacement of the image.

Figure 9:
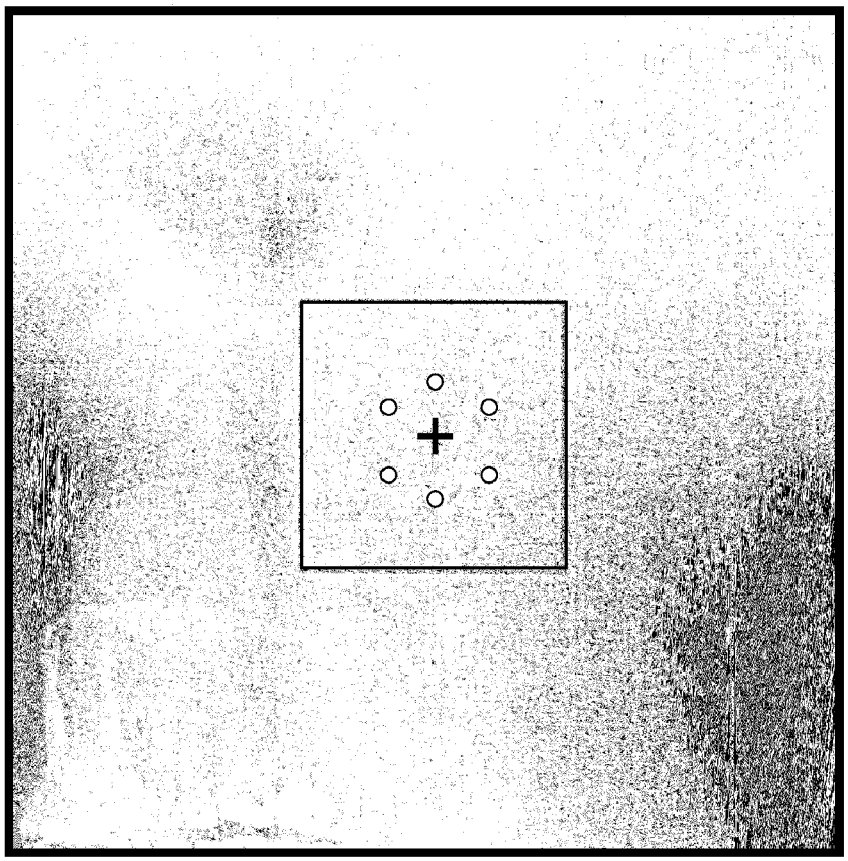
FIG. 9 illustrates global motion estimation between the image center of a DRR and the image center of a corresponding x-ray image.
Figure 9:
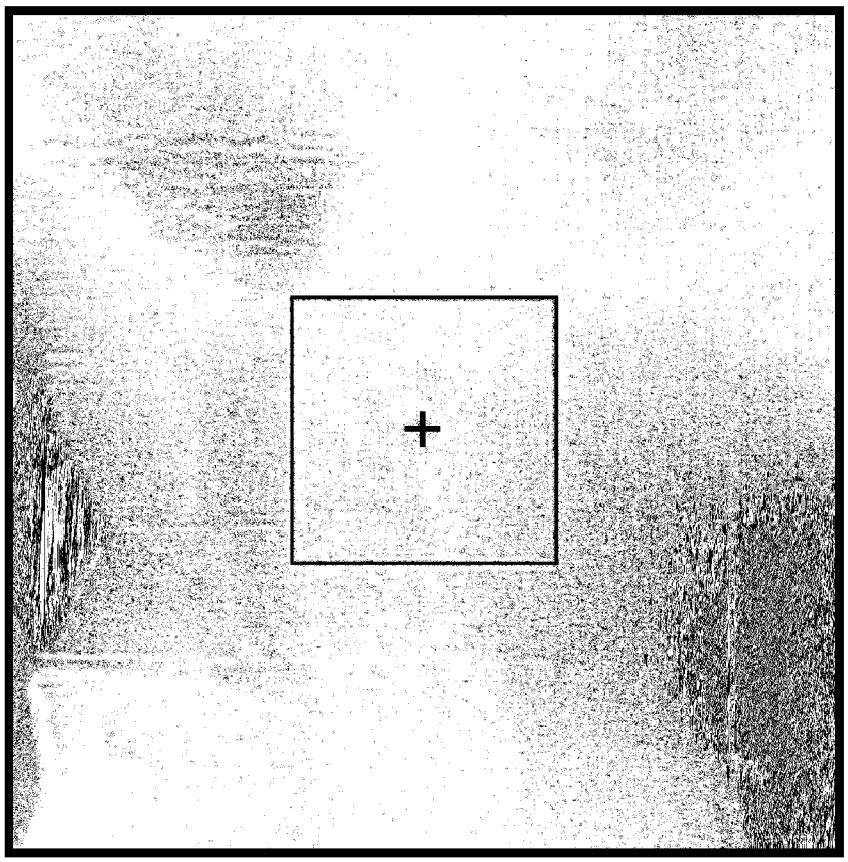

FIG. 9 illustrates the estimation of global motion (in this case, translation only), between the image center of a DRR and the image center of a corresponding x-ray image. In the illustrated embodiment, the image center is used as the block center. The step of global translation estimation is very important, because any failure during this step will affect the rest of the local motion estimation process. To prevent any possibility of mismatching, a very large image block is used in the illustrated embodiment. The maximum tracking range can be calculated as the difference between the block size and the entire image size. For example, if the matching size is 80×80 mm, the maximum tracked translation is 60 mm. In the embodiment illustrated in FIG. 9, a block having a size of 160×160 pixels (64 mm×64 mm) is used. The search window in the illustrated embodiment is the entire image. The maximum track range for the illustrated embodiment is (−50 mm, +50 mm).

After global motion estimation, the next step 130 (see FIG. 2) is mesh motion estimation. In this step, a hierarchical 2D mesh structure is designed in order to estimate local motion in multiple levels. As known, a 2D mesh (or a 2D mesh grid) refers to a tesselation of a 2D region into polygonal patches or elements, whose vertices are called mesh nodes. Unlike block matching algorithms, which generally assume only translational motion, 2D mesh models allow for spatial transformations to model rotations, scalings, and deformations of the object that was imaged, in addition to translations of the object. Compared to block matching algorithms, therefore, mesh-based methods may produce a more accurate representation of the motion field, for example may generate continuously varying motion fields.

Figure 10A:
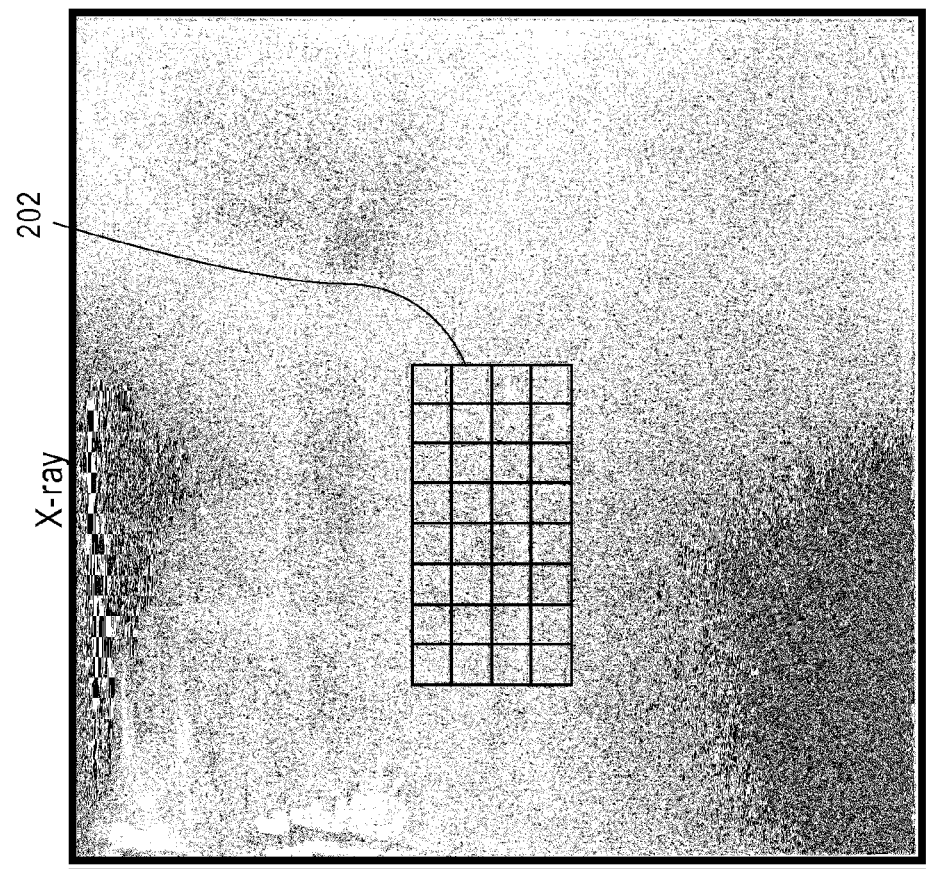
FIG. 10A schematically illustrates a mesh grid established for a DRR of a target region, and a corresponding mesh grid established for an x-ray image of the target region, in an embodiment in which the target is located within the cervical region of the spine.
Figure 10A:
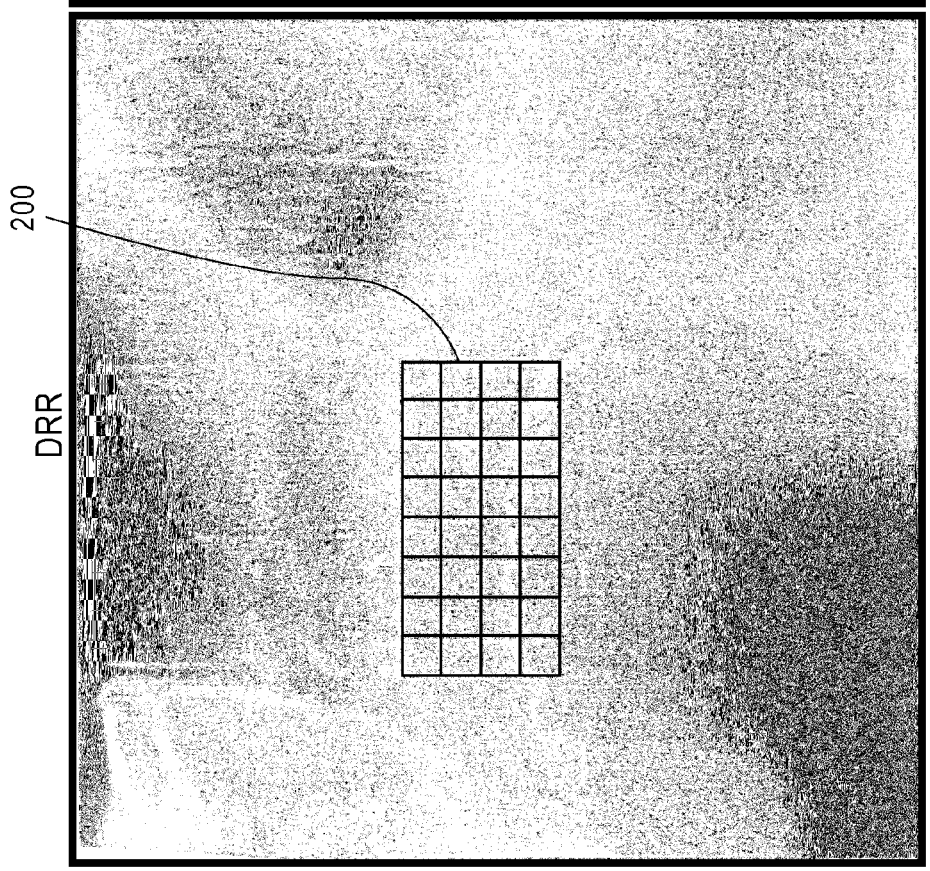
Figure 10B:
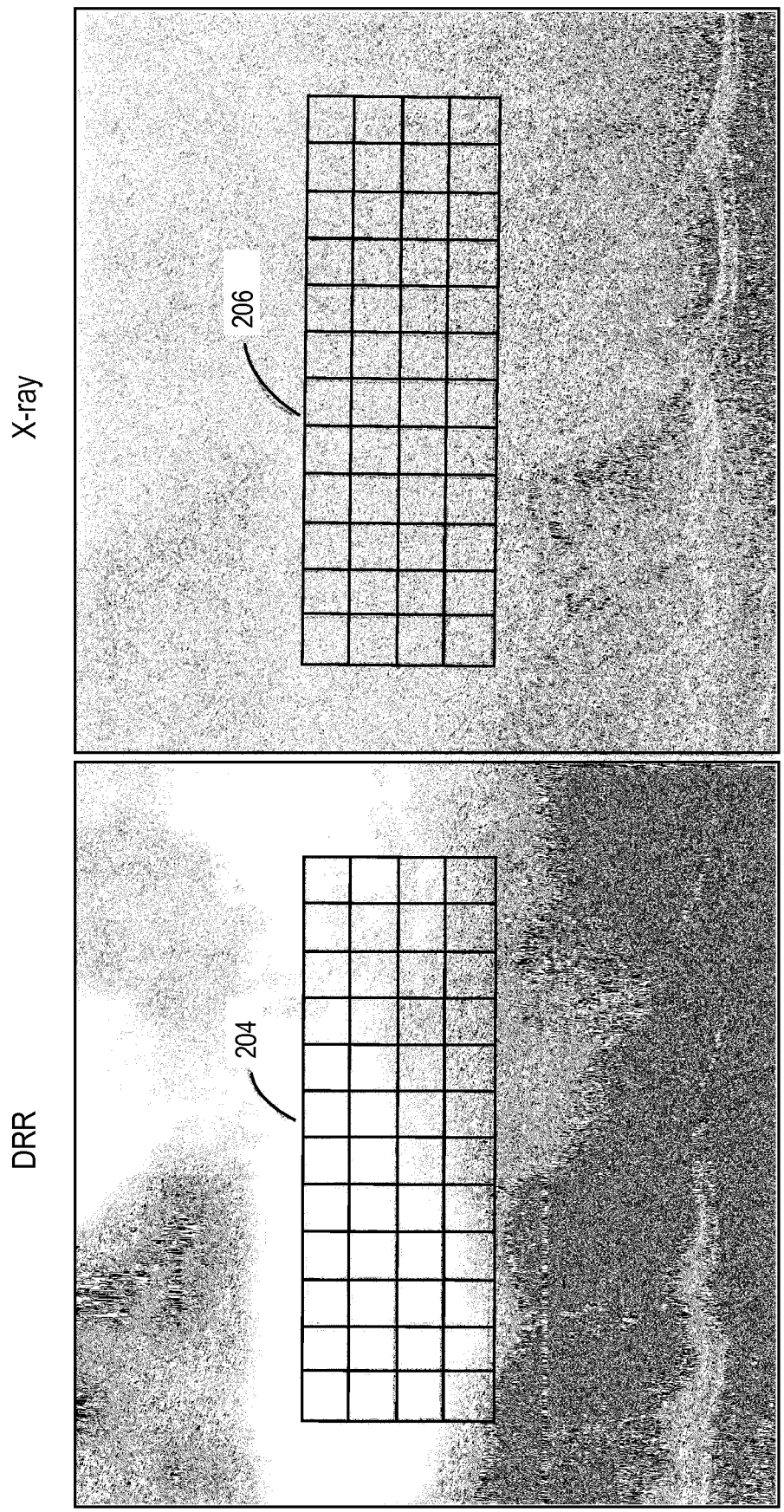
FIG. 10B schematically illustrates a mesh grid established for a DRR of a target region, and a corresponding mesh grid established for an x-ray image of the target region, in an embodiment in which the target is located within the thoracic region of the spine.
Figure 10C:
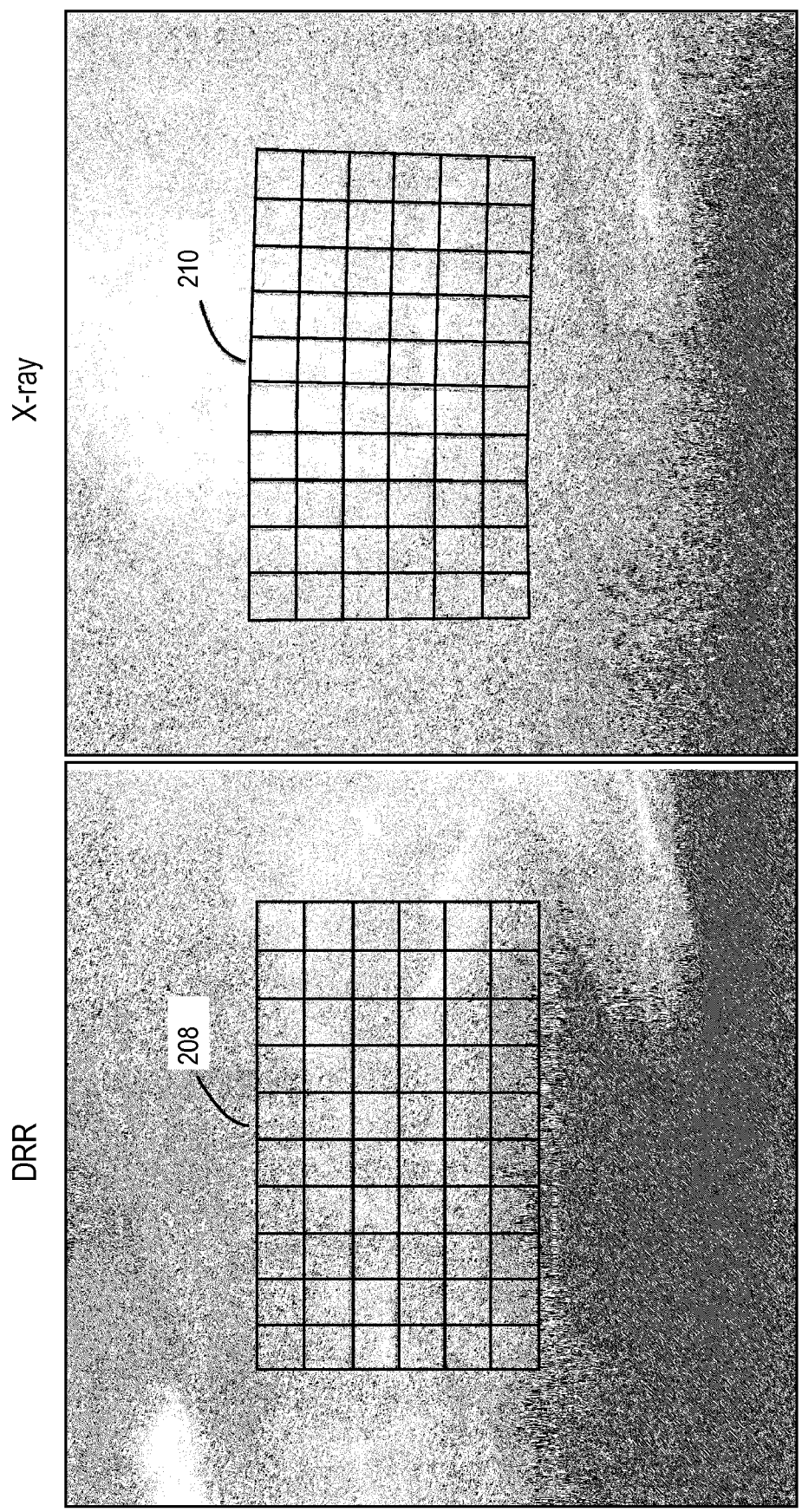
FIG. 10C schematically illustrates a mesh grid established for a DRR of a target region, and a corresponding mesh grid established for an x-ray image of the target region, in an embodiment in which the target is located within the lumbar region of the spine.

FIG. 10A schematically illustrates a mesh grid 200 established for a DRR of a target region, and a corresponding mesh grid 202 established for an x-ray image of the target region, in an embodiment in which the target is located within the cervical region of the spine. FIG. 10B schematically illustrates a mesh grid 204 established for a DRR of a target region, and a corresponding mesh grid 206 established for an x-ray image of the target region, in an embodiment in which the target is located within the thoracic region of the spine. FIG. 10C schematically illustrates a mesh grid 208 established for a DRR of a target region, and a corresponding mesh grid 210 established for an x-ray image of the target region, in an embodiment in which the target is located within the lumbar region of the spine.

With a 2D mesh, motion compensation within each mesh element or patch may be accomplished by deriving a spatial transformation between the images, where the transformation parameters are computed from the nodal motion vectors, i.e. from the motion vectors that are estimated for the mesh nodes that are located at the vertices of the mesh. In other words, mesh-based motion estimation consists of finding a spatial transformation that best maps one set of mesh elements in a first image acquisition onto another set of mesh elements in a second image acquisition. In particular, mesh motion estimation consists of finding the vertices of corresponding mesh elements in the other image, i.e. finding the corresponding mesh nodes in the other image, such that errors are minimized in the overall motion field. Typically, a number of mesh nodes are selected in one image, and the corresponding mesh nodes in the other image are estimated.

For any pixel located within a mesh element (as opposed to being located on the vertices of the mesh elements), the mapping between different image acquisitions is performed through interpolation. The local motion vectors for such pixels are estimated by interpolating from the nodal motion vectors that were estimated for the mesh nodes that surround the pixel.

In one embodiment, hierarchical mesh motion estimation may be performed. By hierarchical mesh motion estimation, it is meant that nodal motion is estimated for the mesh nodes that define the mesh structure, for each of a plurality of mesh resolution levels. Motion estimation performed with a course mesh provides the initialization for the subsequent (finer) resolution levels of the mesh. To estimate the motion of each mesh node, multi-level block matching may be performed.

Figure 11:
FIG. 11 illustrates a hierarchy of meshes for mesh nodal motion estimation, starting from a relatively course mesh and progressing onto finer meshes.

FIG. 11 illustrates a mesh hierarchy, during mesh motion estimation. As seen from FIG. 11, the mesh hierarchy starts from a relatively course mesh, 220, and progresses onto finer meshes, illustrated as 222 and 224. Using the global translations (estimated in step 120 as the initial estimates), nodal motion for the mesh nodes located at the vertices of the most course mesh is first calculated. These estimates are then passed onto the subsequent, finer mesh. At each level, nodal motion is updated, using a smaller search range. Finally, the motion vectors for the mesh nodes at the final one of the mesh resolution levels (characterized by the finest mesh resolution level) are refined. For all the nodes, multi-level block matching with multiple candidates is used, together with the pattern-intensity based similarity measure, given in equations (5) and (6).

FIG. 12 schematically illustrates the passing on of node estimation, from a course mesh resolution level onto a finer mesh resolution level. At each mesh resolution level after the first level, the mesh nodes include both 1) mesh nodes generated at a previous mesh resolution level; and 2) mesh nodes that are newly added at the current mesh resolution level. In the illustrated embodiment, the initial estimates for nodal motion vectors, for the newly added nodes at the current mesh, are obtained by linear interpolation of the existing nodal motion vectors, at the previous mesh resolution level. During this process, any unreliable mesh node needs to be detected, so that only reliable nodes are passed onto the subsequent mesh level.

FIG. 12 illustrates how such a detection can be performed, using a mesh node referred to in FIG. 12 as 'node 5.' In the illustrated embodiment, the difference between the motion vector (in this case, translation vector) of node 5, and the median motions (translations) computed from its 9 surrounding nodes (nodes 1-4, 6-9 in FIG. 12) is taken. As seen from FIG. 12, the translation of node 2 is the average of the translations of node 1 and node 3; the translation of node 4 is the average of the translations of node 1 and node 7; the translation of node 6 is the average of the translations of node 3 and node 9; and the translation of node 8 is the average of the translations of node 7 and node 9. The translation of node 5 is the average of the translations of nodes 1, 3, 7, and 9. If the difference between the translation of node 5 and the median translations computed from its 9 neighboring nodes is less than a predefined threshold, the node 5 is considered as a reliable node. Otherwise, it is considered as an unreliable node, and its translations are replaced with the median values and passed to the subsequent mesh.

For most mesh nodes, the estimates of motion are reliable and accurate. For a few nodes where mismatching may occur and the estimation may not be reliable, the displacements need to be reconstructed by the surrounding node displacements. Accordingly, the next step in the registration algorithm flow chart in FIG. 2 is step 140 of motion field reconstruction, during which the motion field is reconstructed from surrounding nodes, for those nodes in which mismatching occurs. The inaccurate nodal motion vectors can be detected by using 3×3 median filtering.

Local motion estimation relies on the local image content. In some smooth local regions, mismatching may occur. During mesh motion estimation, the estimation in most nodes is pretty accurate. For a few nodes where mismatching occurs, the motions should be reconstructed from their surrounding nodes. What is known a priori is matter coherence of bone and tissue, and accordingly, the smoothness of local motion. In other words, the estimated local motion vectors are thought to be smooth and continuous, because of matter coherence. By imposing this physically-based smoothness constraint, a cost function is formulated to reconstruct the motion field.

In one embodiment, the cost function is expressed mathematically as follows:

$$E(d) = \iint \beta (d-u)^2 dx dy + \lambda \iint (d_x^2 + d_y^2) dx dy \quad (7)$$

In equation (7) above, E(d) represents the cost function, d represents a desired local estimate for a nodal motion vector at coordinates (x,y), u represents a locally estimated nodal motion vector at coordinates (x,y), and $\beta$ represents a reliability constant that ranges from 0 to 1, where $\beta=0$ indicates an unreliable estimation, and $\beta=1$ indicates a reliable estimation.

By performing a finite difference of the derivatives over the mesh grids, a discretized form for the cost function in equation (7) is expressed as:

$$E(d_{i,j}) = \Sigma\Sigma \beta_{i,j}(d_{i,j}-u_{i,j})^2 + \lambda\Sigma\Sigma[(d_{i,j}-d_{i-1,j})^2 + (d_{i,j}-d_{i,j-1})^2] \quad (8)$$

where $u_{i,j}$ represents the locally estimated translations, $d_{i,j}$ is the local motion desired, $\beta_{i,j}=1$ if the estimation is reliable and $\beta_{i,j}=0$ if the estimation is unreliable.

The first term on the right side of equation (8) reflects the fidelity to the observed data in the reconstruction. The second term imposes the smoothness constraints on the motion field in two spatial directions.

The minimization of the cost function given by equation (8) results in a system of simultaneous linear equations $$\frac{\delta E(d_{i,j})}{\partial d_{i,j}} = (\beta_{i,j} + 4\lambda)d_{i,j} - \lambda(d_{i-1,j} + d_{i+1,j} + d_{i,j-1} + d_{i,j+1}) - \beta_{i,j}u_{i,j} = 0 \quad (9)$$

In one embodiment, the iterative algorithm of successive-over relaxation (SOR), which is fast and convergent, is used to solve the equations:

$$d_{i,j}^{(n+1)} = d_{i,j}^{(n)} - \omega[(\beta_{i,j}+4\lambda)d_{i-1,j}^{(n)} - \lambda(d_{i-1,j}^{(n)}+d_{i+1,j}^{(n)}+d_{i,j-1}^{(n)}+d_{i,j+1}^{(n)}) - \beta_{i,j}u_{i,j}]/(\beta_{i,j}+4\lambda) \quad (10)$$

Figure 13:
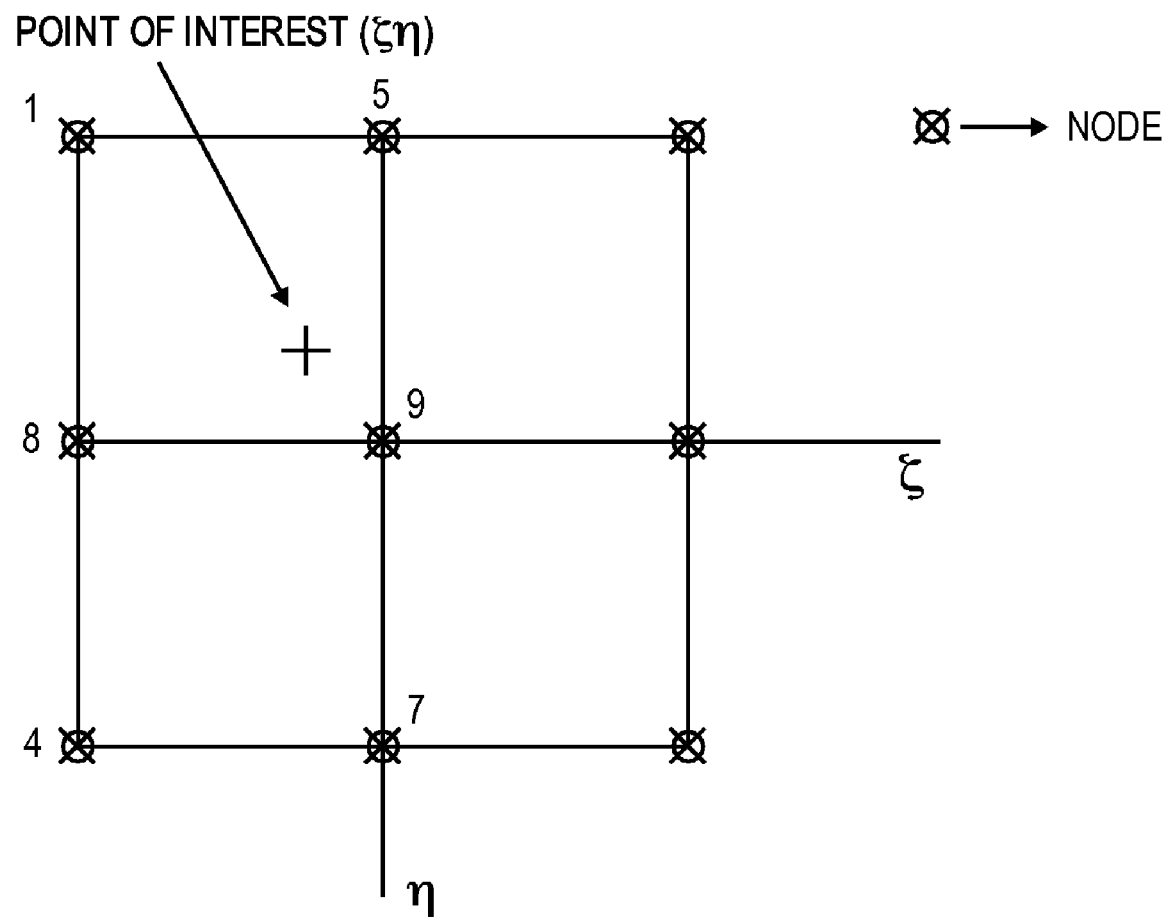
FIG. 13 schematically illustrates the determination of a motion vector for a point of interest, by interpolation from surrounding nodes.

Once all the nodal motion vectors have been estimated at all the mesh nodes, the translations for any point (or pixel) inside the ROI can be computed by interpolation. FIG. 13 schematically illustrates the determination of a motion vector for a point of interest, by interpolation from surrounding nodes. In the illustrated embodiment, quadratic interpolation is performed, using the 9 nearest nodes, and 9 shape functions are used.

Assuming the motion vector (dx(i), dy(i)) for nine nodes, the motion vector (dx, dy) at the point of interest is computed using the following expressions:

$$dx = \sum_{i=1}^{9} N(i)dx(i), \quad (11)$$

$$dy = \sum_{i=1}^{9} N(i)dy(i),$$

where N(i) is the shape function for the node (i), and where N(i) for I=1, 2, . . . 9 are given as follows:

$$N(1)=(1-\xi)(1-\eta)/4-(N_8+N_5)/2,$$

$$N(2)=(1-\xi)(1-\eta)/4-(N_5+N_6)/2,$$

$$N(3)=(1+\xi)(1+\eta)/4-(N_6+N_7)/2,$$

$$N(4)=(1-\xi)(1+\eta)/4-(N_7+N_8)/2,$$

$$N(5)=(1-\xi^2)(1-\eta)/2,$$

$$N(6)=(1-\xi)(1-\eta^2)/2,$$

$$N(7)=(1-\xi^2)(1+\eta)/2,$$

$$N(8)=(1-\xi)(1-\eta^2)/2,$$

$$N(9)=(1-\xi^2)(1-\eta^2).$$

Using steps 120, 130, and 140, described above, the local motion vectors can be estimated for a plurality of points of interest within the ROI. The full motion field is obtained as a composite or superposition of all of the local motion vectors that are estimated for the many points of interest that have been selected for motion estimation.

Figure 14A:
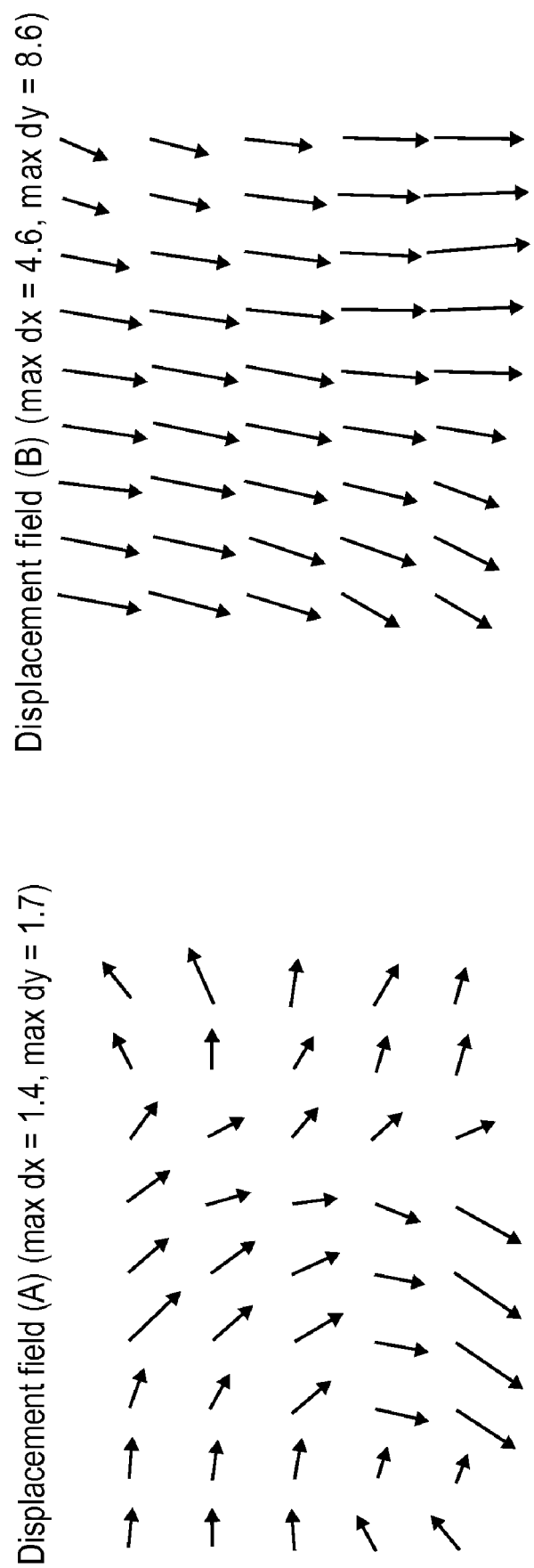
FIG. 14A schematically illustrates, in vectorial form, a full motion field (reconstructed from many estimated local motion vectors), in an embodiment in which the target is located within the cervical region of the spine.
Figure 14B:
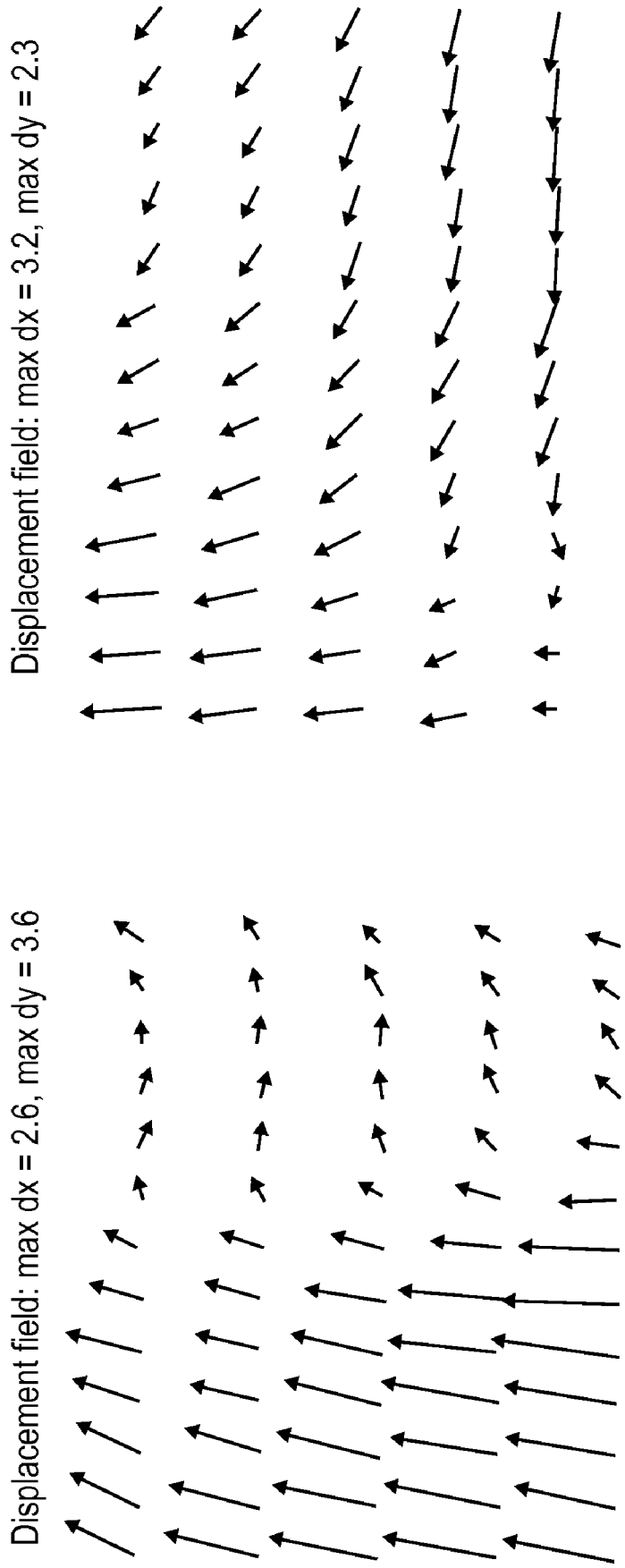
FIG. 14B schematically illustrates, in vectorial form, a full motion field (reconstructed from many estimated local motion vectors), in an embodiment in which the target is located within the thoracic region of the spine.
Figure 14C:
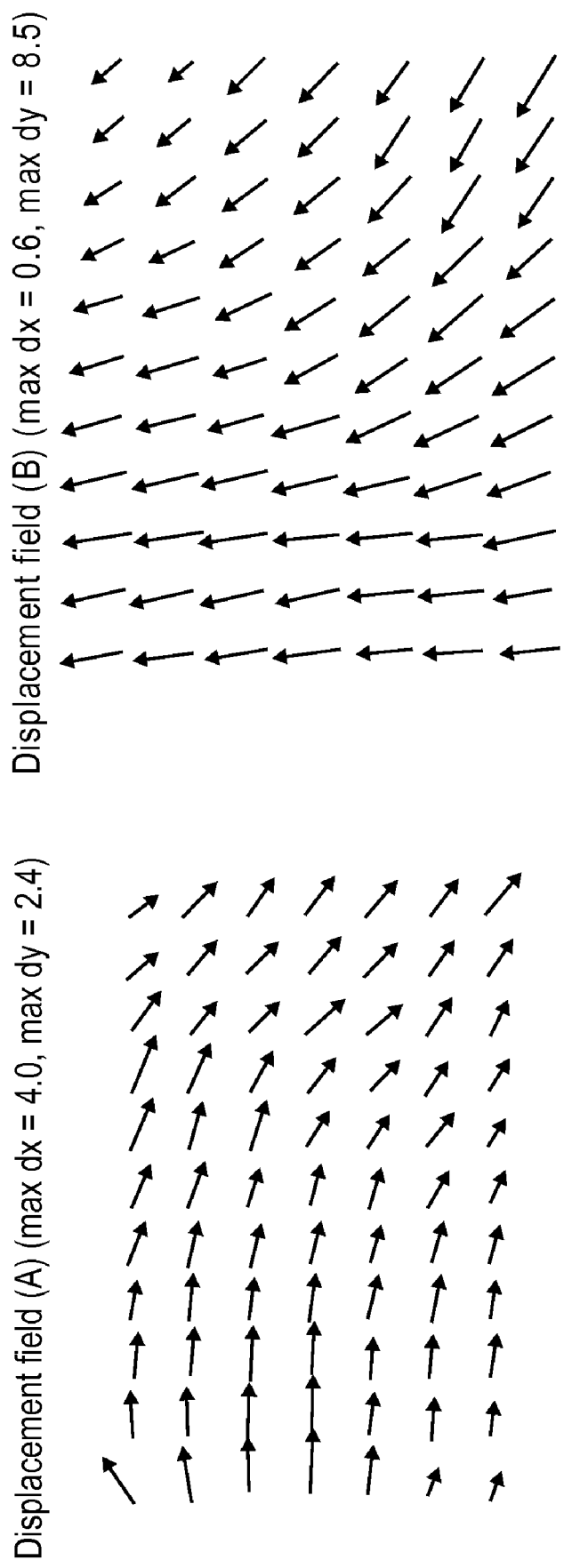
FIG. 14C schematically illustrates, in vectorial form, a full motion field (reconstructed from many estimated local motion vectors), in an embodiment in which the target is located within the lumbar region of the spine.

FIG. 14A schematically illustrates, in vectorial form, a full motion field (reconstructed from many estimated local motion vectors), in an embodiment in which the target is located within the cervical region of the spine. FIG. 14B schematically illustrates, in vectorial form, a full motion field (reconstructed from many estimated local motion vectors), in an embodiment in which the target is located within the thoracic region of the spine. FIG. 14C schematically illustrates, in vectorial form, a full motion field (reconstructed from many estimated local motion vectors), in an embodiment in which the target is located within the lumbar region of the spine.

The final step in the image registration process is target localization, namely deriving the target translations and rotations from the full motion field that has been determined. In one embodiment, non-rigid image registration seeks to determine a projection mapping or transformation between different coordinate systems in respective image acquisitions such that points in each space which correspond to the same anatomical point are mapped to each other. In one embodiment, the transformation is represented by a set of non-rigid transformation parameters $(dx_T, dy_T, dz_T, r, p, w)$, where $(dx_T, dy_T, dz_T)$ represent the translations of the target, and $(r, p, w)$ represent rotations of the target.

Referring back to FIG. 2, the 3-D target translation $(dx_T, dy_T, dz_T)$ can easily be obtained in step 155 (shown in FIG. 1), given the 2D local motion fields $(dx_A, dy_A)$ for projection A, and $(dx_B, dy_B)$ for projection B, using the following expressions:

$$dx_T = (dx_{TA} + dx_{TB})/2, \quad (13)$$

$$dy_T = (dy_{TA} - dy_{TB})/\sqrt{2},$$

$$dz_T = (dy_{TA} + dy_{TB})/\sqrt{2}$$

The global rigid rotations $(r, p, w)$ can be calculated from the motion fields $(dx_A, dy_A)$ in projection A and $(dx_B, dy_B)$ in projection B. Using the target as the rotation center, global rigid rotations are useful for position and rotation correction and compensation during initial patient alignment and treatment. Because the target translation is already calculated, the calculation of the global translation is not needed. To get the three rotations in 3D patient coordinates, three 2D in-plane rotations are first computed, including the in-plane rotations $\theta_A$ and $\theta_B$ in projections A and B, respectively, and the in-plane rotation $\theta_x$ in a plane perpendicular to the inferior-superior axis. Approximately, the global rotations can be expressed as:

$$r = \theta_x, \quad (14)$$

$$p = (\theta_B - \theta_A)/\sqrt{2},$$

$$w = (\theta_B + \theta_A)/\sqrt{2},$$

Estimation of $\theta_A$ and $\theta_B$ is directly based the 2D motion fields in projections A and B, respectively. To estimate $\theta_x$, a plane is first defined, which passes the target point and is perpendicular to the axis x in the 3D patient coordinate system. Then the motion field is calculated from the two motion fields $(x_A, y_A)$ and $(x_B, y_B)$ in projections A and B, respectively.

Assuming $(dx, dy)$ is the motion field in the corresponding coordinate $(x, y)$ and $\theta$ is the global rotation. When the rotation is small ($<10°$), the following transformation equation is valid:

$$\begin{Bmatrix} dx \\ dy \end{Bmatrix} = \begin{bmatrix} 0 & -\theta \\ \theta & 0 \end{bmatrix} \begin{Bmatrix} x \\ y \end{Bmatrix} \quad (15)$$

Given $(dx,dy)$ and $(x,y)$ in many points, $\theta$ can be easily calculated using least square minimization method $$\theta = \frac{\sum_i (x(i)dy(i) - y(i)dx(i))}{\sum_i (x(i)x(i) + y(i)y(i))} \quad (16)$$

Using equations (14) and (16) above, the average rigid transformation parameters can be obtained, in step 160 illustrated in FIG. 2.

Figure 15:
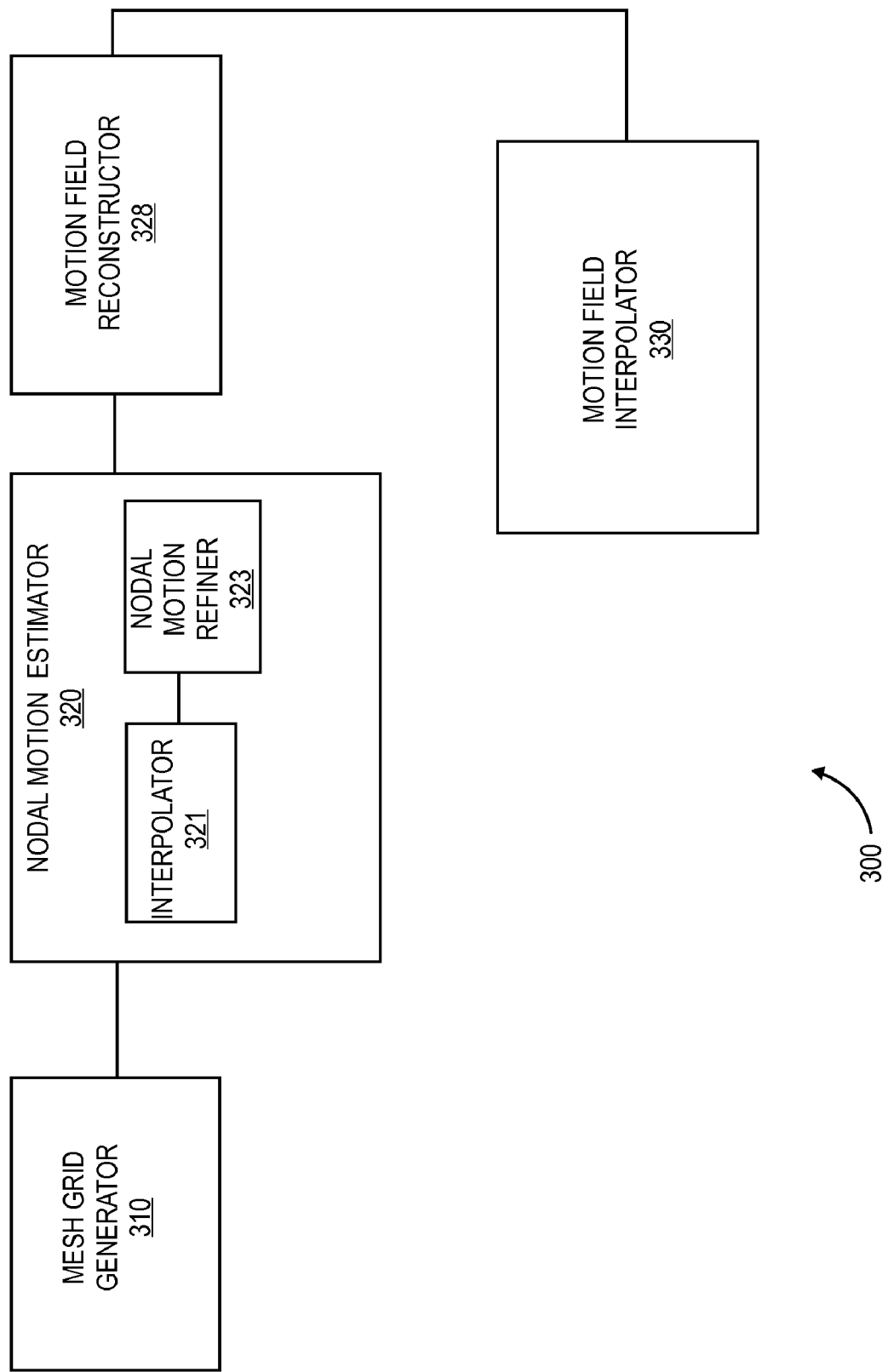
FIG. 15 is a schematic block diagram of a motion field generator configured to generate a full motion field during non-rigid image registration of an object, in accordance with one embodiment.

FIG. 15 is a schematic block diagram of an apparatus 300 for generating a motion field during non-rigid image registration of an object, in accordance with one embodiment. The apparatus 300 can generate, for example, a full motion field of a target region of a patient's anatomy (for example, the spine), between the acquisition of pre-operative 3D scan data of the target region and the acquisition of intra-operative x-ray projection images of the target region. The full motion field, composed of many local motion vectors, can take into account non-rigid deformations of the target region, as well as non-rigid translations and rotations. In this embodiment, the 2D/3D registration problem is one of finding the non-rigid transformation parameters that best align the coordinate system of the DRRs (generated from the pre-operative 3D scan data) with that of the intra-operative x-ray projection images.

In one embodiment, the apparatus 300 is configured to perform mesh motion estimation, and to perform multi-level block matching at each mesh node. In this embodiment, the apparatus 300 includes: 1) a mesh grid generator 310 configured to generate in the DRRs a mesh grid defined by a plurality of mesh nodes or vertices; 2) a nodal motion estimator 320 configured to estimate at least one nodal motion vector for each mesh node; and 3) a motion field interpolator 330 configured to determine a local motion vector for each of a plurality of points of interest within the DRR, by interpolating from the surrounding mesh nodes, i.e. by interpolating from the nodal motion vectors that have been estimated for the mesh nodes that surround each of the plurality of points of interest. In an embodiment in which the DRR has been cropped so as to include a specific ROI, so that image registration is restricted to an ROI within the DRR, the motion field interpolator 330 determines the local motion vectors for each of a plurality of points of interest within an ROI defined within the DRR. The ROI can be defined so as to maximize image entropy within the ROI, as explained before.

In one embodiment, the system 300 performs hierarchical mesh tracking, i.e. mesh nodal motion estimation is performed for the mesh nodes of the mesh structures defined at each of a plurality of mesh resolution levels. Preferably, these mesh resolution levels are successively increasing mesh resolution levels, i.e. the mesh grid at each successive mesh resolution level has a number of mesh nodes that is greater, compared to the number of mesh nodes at each previous mesh resolution level. In this embodiment, the mesh grid generator 310 is configured to repeat, at each of a plurality of mesh resolution levels, the act of generating a mesh grid defined by a plurality of mesh nodes, and the nodal motion estimator 320 is similarly configured to repeat, at each of a plurality of mesh resolution levels, the act of estimating the nodal motion vector for each mesh node. In this embodiment, the motion field interpolator interpolates from nodal motion vectors that have been determined at the final mesh resolution level.

In one embodiment, the mesh nodes at each mesh resolution level after the first level include both previously existing nodes, and nodes that are newly added on, at the current level. In this embodiment, the nodal motion estimator 320 is configured to pass on, at each mesh resolution level, one or more nodal motion vectors that have been estimated at the current mesh resolution level, onto a subsequent mesh resolution level. In particular, for the previously existing nodes, the nodal motion estimator 320 uses the nodal motion vectors that were estimated during a previous mesh resolution level, and that were passed onto the current level from the previous level. The nodal motion estimator 320 includes an interpolator 321, which interpolates from the nodal motion vectors estimated for the previously existing nodes, in order to estimate the nodal motion vectors for the newly added nodes. The nodal motion estimator 320 further includes a nodal motion refiner 323. For both previously existing nodes and newly added nodes, the nodal motion refiner 323 refines the nodal motion vector that has been estimated for each node.

In one embodiment, the nodal motion refiner 323 refines the nodal motion vector by performing multi-level block matching, using a pattern-intensity based similarity measure. In this embodiment, the nodal motion refiner 323 defines a block centered on each mesh node in the DRR, and searches for a matching mesh node in the x-ray projection image that maximizes a similarity measure between the block in the DRR, and a matching block in the x-ray image that is centered on the matching mesh node. In one embodiment, the similarity measure is given by equations (5) and (6) above. The nodal motion refiner 323 then refines and modifies the nodal motion vector that was estimated for the particular mesh node, until the nodal motion vector describes a mapping of the mesh node onto the matching mesh node.

In one embodiment, the nodal motion refiner 323 performs multi-level block matching, i.e. repeats for a plurality of image resolution levels the acts of defining a block centered on the mesh node of interest, searching for the matching mesh node, and refining the nodal motion vector. In one embodiment, the nodal motion refiner 323 defines a search window around the mesh node of interest, and searches within the search window for a maximum in the similarity measure. Because several local maximums may exist, in addition to the desired global maximum, the nodal motion refiner 323 preferably reviews a plurality of candidates when searching for the location of the maximum in the similarity measure.

In one embodiment, the nodal motion estimator 320 is configured to estimate a global translation of the DRR, and to use the global translation as an estimate for the nodal motion vector for each mesh node in the first mesh resolution level. The global translation represents a translation of the image center of the DRR.

In one embodiment, the apparatus 300 further includes a motion field reconstructor 328. The motion field reconstructor 328 is configured to reconstruct the nodal motion vector for any mesh node at which mismatching occurs, i.e. for which the estimated nodal motion vector is unreliable. The motion field reconstructor 328 reconstructs such unreliable nodal motion vectors by interpolating from the mesh nodes that surround the unreliable mesh node. In this embodiment, the nodal motion estimator 320 computes the difference between the nodal motion vector for a mesh node, and the median nodal motion vector computed from its surrounding 9 nodes. If the difference is less than a predefined threshold, the node is considered as a reliable node, otherwise it is considered as an unreliable node. The nodal motion vector for an unreliable node is replaced with the median values, and passed on to the subsequent mesh.

In one embodiment, the motion field reconstructor 328 reconstructs nodal motion vectors for unreliable nodes by imposing a smoothness constraint on the nodal motion vectors estimated by the nodal motion estimator 320. In one embodiment, the motion field reconstructor 328 imposes the smoothness constraint by formulating a cost function given by equation (8) above, and minimizing the cost function by solving the system of linear equations, as expressed in equation (9).

In one embodiment, the motion field interpolator 330 interpolates, for any desired point of interest within the ROI of the DRR, the local motion vector for the point of interest by interpolating from the nodal motion vectors estimated for the surrounding mesh nodes, by performing the summation described in equations (6) and (7).

The apparatus 300 may include a computer-readable medium having stored therein computer-readable instructions for a processor. These instructions, when read and implemented by the processor, cause the processor to: 1) input and store, for a first image of an object, data representative of a mesh grid having a plurality of mesh nodes, for each of a plurality of mesh resolution levels; 2) estimate, for each mesh node in each mesh resolution level, at least one nodal motion vector that describes a matching of the mesh node onto a corresponding mesh node in a second image; and 3) compute a local motion vector for one or more points of interest in the first image by interpolating from the nodal motion vectors estimated at a final mesh resolution level for the mesh nodes that surround each point of interest.

The computer-readable medium may have stored therein further computer-readable instructions for the processor. These further instructions, when read and implemented by the processor, cause the processor to detect any mesh node for which a mismatch occurs between the mesh node (in the first image) and its corresponding mesh node (in the second image), and to reconstruct the nodal motion vector for the detected mesh node by imposing a smoothness constraint. The computer-readable medium may be any medium known in the art, including but not limited to hard disks, floppy diskettes, CD-ROMs, flash memory, and optical storage devices. The computer readable instructions described above may be provided through software that is distributed through the Internet.

Figure 16:
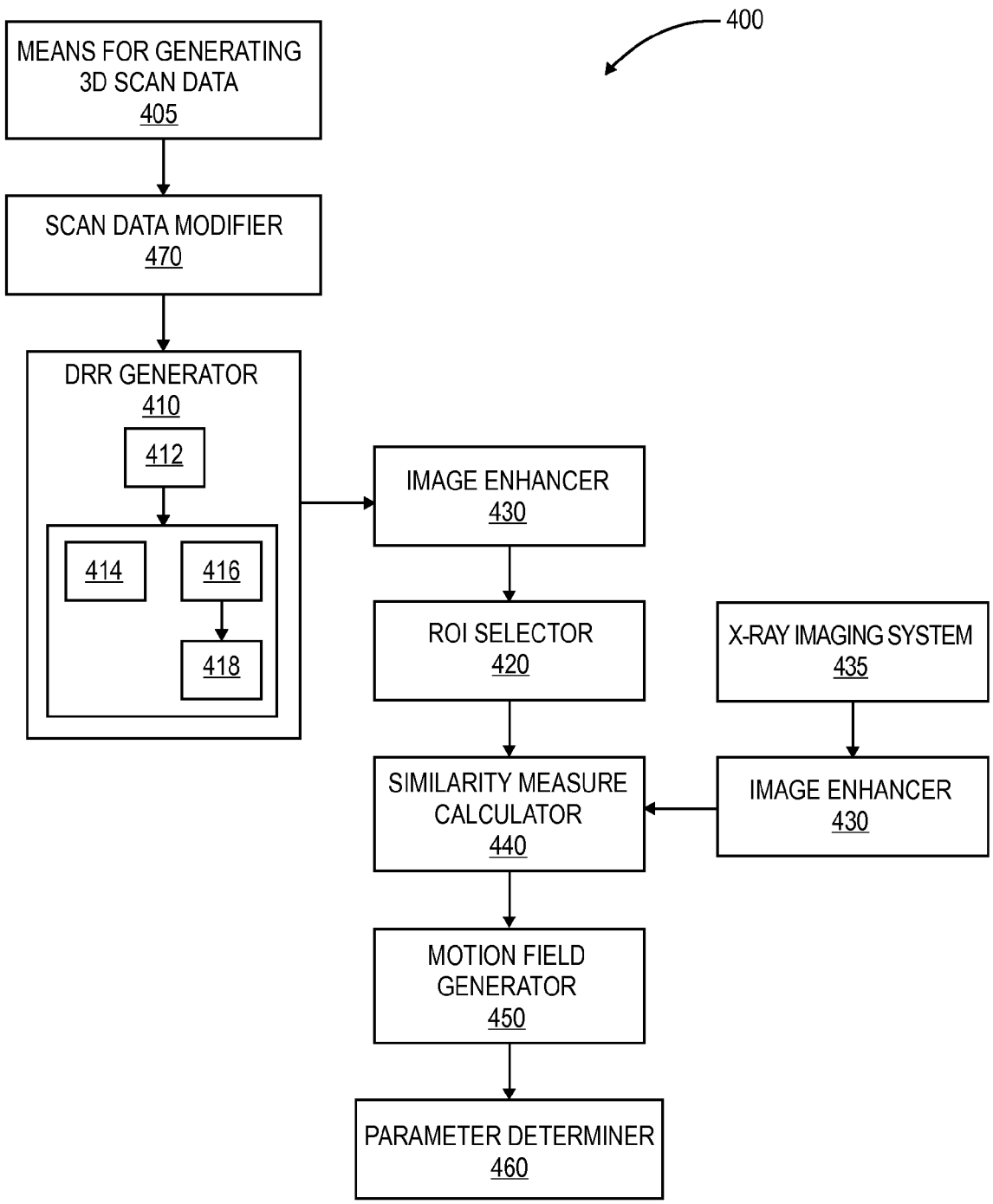
FIG. 16 is a schematic block diagram of an apparatus for performing fiducial-less non-rigid image registration, in one embodiment.

FIG. 16 is a schematic block diagram of a system 400 for performing fiducial-less non-rigid image registration, in accordance with one embodiment. The image registration system 400 can register at least one near real time 2D image of an anatomical region with previously generated 3D scan data of the anatomical region. The anatomical region includes at least one treatment target and at least one reference structure, typically a skeletal or vertebral structure. The near real time 2D images are generated by detecting imaging beams (e.g. x-ray imaging beams) that have known intensities, and known positions and angles relative to the anatomical region, after the beams have traversed at least a portion of the anatomical region. The system 400 also includes an x-ray imaging system 435 that generates imaging beams having these known intensities and originating from these known positions and angles.

The system 400 includes means 405 for providing the 3D scan data of the anatomical region. The 3D scan data may be CT scan data provided by a CT scanner. Alternatively, MRI scan data, provided by an MRI system, may be used. Alternatively, PET scan data, provided by a PET system, may be used. In these different embodiments, the means 305 for providing 3D scan data may include, but is not limited to, a CT scanner, an MRI system, and a PET system, respectively. The system 400 includes a DRR generator 410 configured to generate at least one DRR (digitally reconstructed radiograph) of the anatomical region, using the 3D scan data and the known locations, angles, and intensities of the imaging beams.

The system 400 further includes: 1) an ROI selector 420 configured to select an ROI (region of interest) within the DRR, the ROI containing the treatment target and preferably at least one reference structure; 2) an image enhancer 430 configured to enhance the DRRs and the x-ray images by applying a filter operator to the DRR and to the x-ray image; 3) a similarity measure calculator 440 configured to determine a measure of similarity between the DRR and the x-ray image; 4) a motion field generator 450 configured to generate a 3D full motion field by estimating, for each of a plurality of resolution levels, one or more 2D local motion fields within the ROI, using the similarity measure; and 5) a parameter determiner 460 configured to determine a set of non-rigid transformation parameters that represent the difference in the position and orientation of the treatment target as shown in the x-ray image, as compared to the position and orientation of the treatment target as shown in the DRR, from the 3D full motion field.

In an embodiment in which CT data are used, the 3D scan data consist of a plurality of CT numbers representing the image intensity of corresponding 3D CT voxels, where each CT voxel represents a corresponding volume element of the anatomical region, and each CT number represents the attenuated intensity of an x-ray CT beam that has been generated at a CT scan energy level and that has traversed the corresponding volume element of the anatomical region.

The system 400 further includes a scan data modifier 470, configured to modify the 3D scan data before the 3D scan data are used by the DRR generator 410, so as to compensate for the difference between the ratio of bone-to-tissue attenuation at the CT scan energy level, and the ratio of bone attenuation at the x-ray projection energy level, i.e. at the known intensity level of the imaging beam. The scan data modifier 470 includes a processor for performing on each CT number a mathematical operation derived from a non x-ray attenuation model, where the mathematical operation is given by:

$$C(x,y,z) = aC_0(x,y,z)e^{bC_0(x,y,z)}$$

In this formula, $C(x,y,z)$ represents the modified CT number of a 3D CT voxel having a location $(x,y,z)$; a and b represent weighting coefficients; and $C_0(x,y,z)$ represents the unmodified CT number, based on a linear attenuation model, of a 3D CT voxel having a location $(x,y,z)$.

In one embodiment, the DRR generator 410 includes: 1) a ray casting subsystem 412 configured to cast a plurality of hypothetical rays through the 3D CT voxels, at the known intensities and from the known positions and angles; 2) a CT number integrator 414 for integrating along each hypothetical ray the CT numbers corresponding to the CT voxels that are traversed by the hypothetical ray; 3) a projector 416 for projecting the integrated values of the CT numbers onto an imaging plane.

In one embodiment, the CT number integrator 414 includes a bi-linear interpolator 416 configured to perform bi-linear interpolation on the voxels encountered by each ray, and a polynomial interpolator 418 configured to perform, for each voxel of interest within a voxel slice, a one-dimensional polynomial interpolation over the voxel of interest and over voxels on each adjacent voxel slice. Bi-linear interpolation, as well as 1-D polynomial interpolation, are well known, and standard software and/or algorithms that are commercially available may be used.

In one embodiment, the filter operator applied by the image enhancer 430 is a top-hat filter, configured to select the pixel having the brightest pixel value from each of at least two different neighborhoods within the DRR and the x-ray image, and to eliminate the remaining pixels in the neighborhoods. Mathematically, the top hat filter is defined by equation (2) above.

In one embodiment, the ROI selector includes an entropy calculator that calculates a modified Shannon entropy of the DRR. The modified Shannon entropy is given by: $H = -\Sigma_I I P(I) \log P(I)$, where I is the value of the intensity of the image, at each pixel of the image, and P(I) is the probability of an image intensity value I occurring within the ROI. The ROI selector further includes region selecting processor for selecting the ROI so that the entropy measure H is maximized within the ROI. Calculation of Shannon entropy is well known in signal processing. Also well known is maximizing (or minimizing) an entropy function, for desired purposes. Therefore, standard software and/or algorithms that are commercially available may be used in the ROI selector 420, with only minimal trivial revisions to incorporate the modification indicated in the formula for modified Shannon entropy.

In one embodiment, the similarity measure calculator 440 is configured to form a difference image by subtracting a corresponding pixel value of the DRR from each pixel value of the near real time (or "live") x-ray image, so that the pixel value at the i-th row and j-th column of the array of pixel values for the difference image is given by:

$$I_{dif}(i,j) = I_{Live}(i,j) - I_{DRR}(i,j).$$

The similarity measure calculator 440 is also configured to apply upon each pixel of the difference image a pattern intensity function, defined by summing asymptotic functions of the gradients of the difference image over the pixels within a neighborhood R. R is defined so that the gradients of the difference image can be considered in at least four directions: a) a substantially horizontal direction; b) a substantially vertical direction; c) a substantially diagonal direction at about 45 degrees; and d) a substantially diagonal direction at about −45 degrees. The pattern intensity function is characterized by a mathematical formulation given by equations (5) and (6) above.

The details of the motion field generator 450 have been fully described above in conjunction with FIG. 15. In one embodiment, the parameter determiner 460 is configured to determine a separate set of transformation parameters for each of pair of orthogonal projection x-ray image, formed by projecting the anatomical region onto respective projection image planes. In this embodiment, the non-rigid transformation parameters include three translational parameters (x, y, and z), and three rotational parameters (r, p, w), where (x, y, and z) represent the three translations of the treatment target along the directions of three mutually orthogonal x-, y-, and z-axes, respectively; and where (r, p, w) represent the three rotations (roll, pitch, yaw) of the treatment target about the three mutually orthogonal x-, y-, and z-axes. The parameter determiner 460 is further configured to combine the resulting parameters for each projection to obtain the 3D transformation parameters. The 3D transformation parameters are related to the transformation parameters for projections A and B by the following relationship:

$$x=(x_A+x_B)/2, y=(y_A-y_B)/\sqrt{2}, z=(y_A+y_B)\sqrt{2},$$

$$r=\theta_x, p=(\theta_B-\theta_A)/\sqrt{2}, w=(\theta_B+\theta_A)/\sqrt{2} \quad (17)$$

Figure 17A:
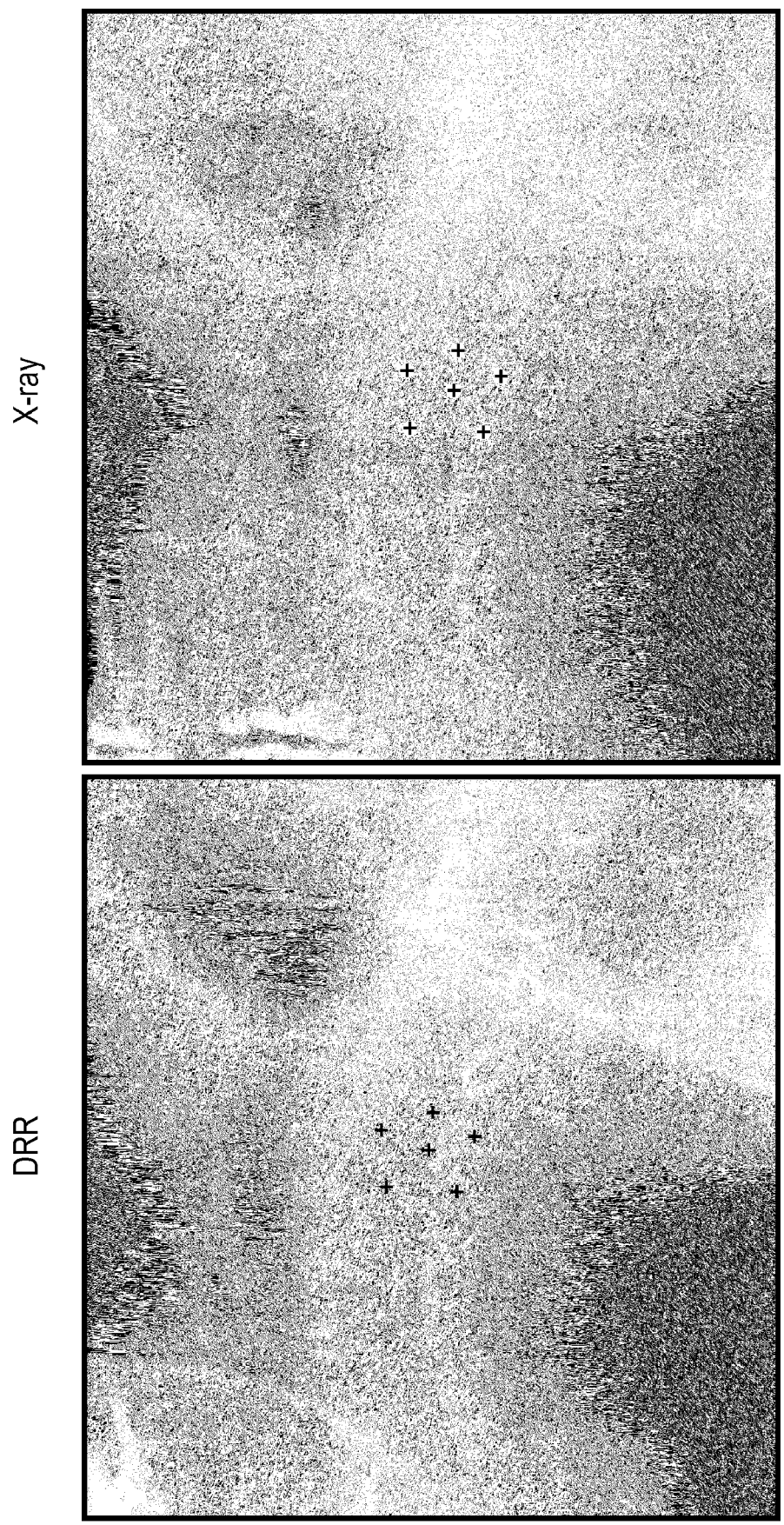
FIG. 17A schematically illustrates target localization between a DRR of the target and an x-ray image of the target, in an embodiment in which the target is located within the cervical region of the spine.
Figure 17B:
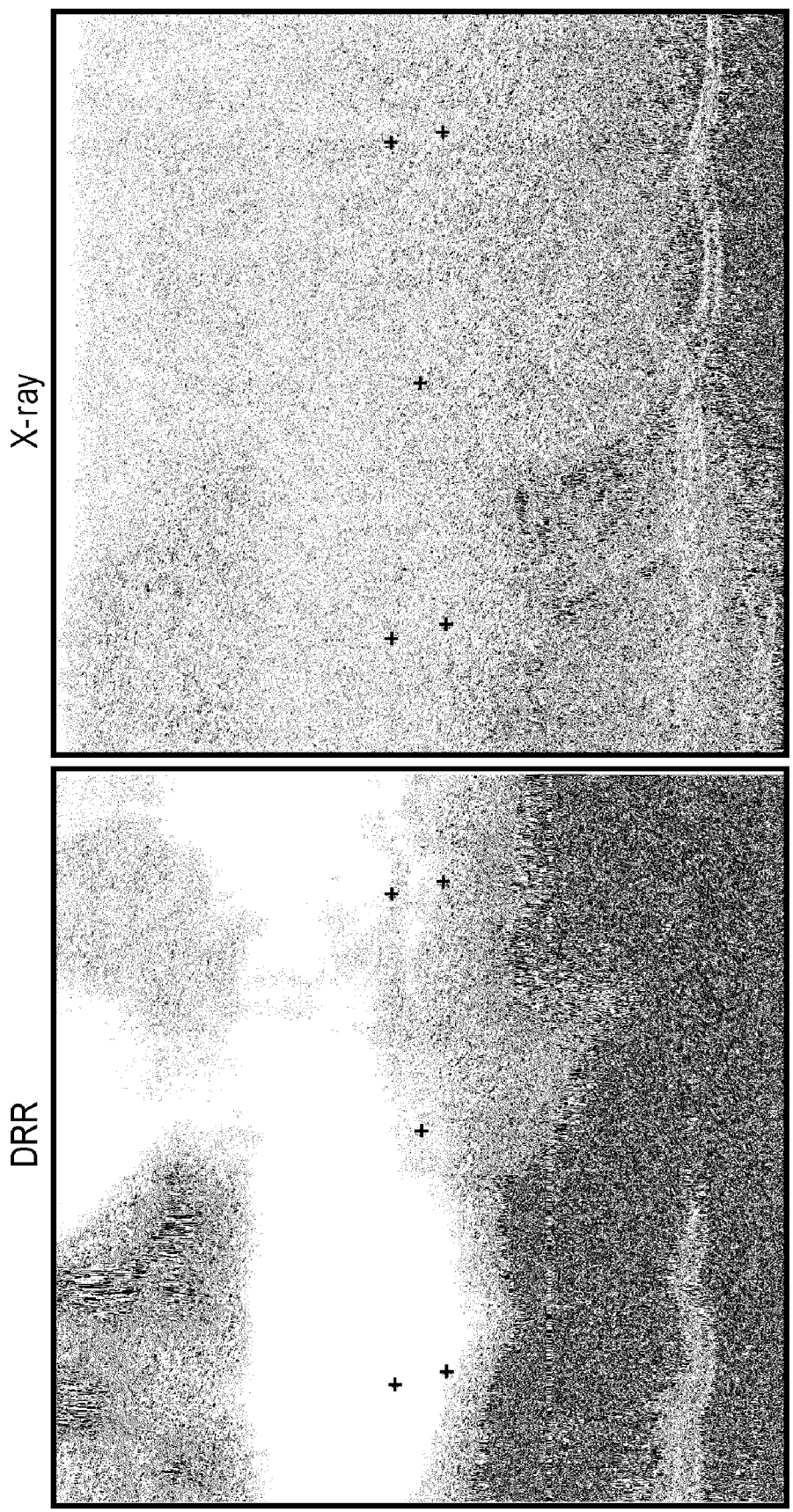
FIG. 17B schematically illustrates target localization between a DRR of the target and an x-ray image of the target, in an embodiment in which the target is located in the thoracic region of the spine.
Figure 17C:
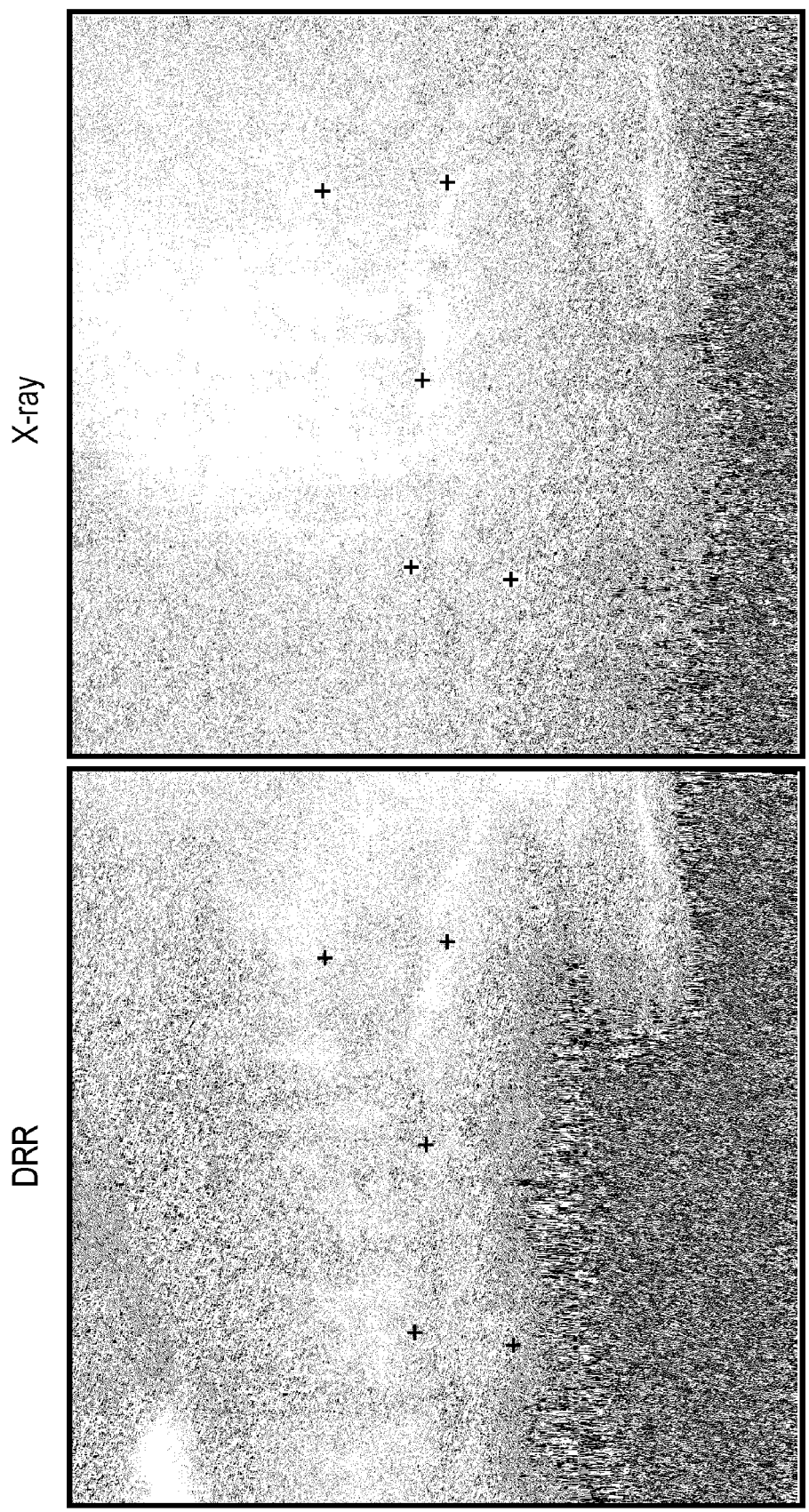
FIG. 17C schematically illustrates target localization between a DRR of the target and an x-ray image of the target, in an embodiment in which the target is located in the lumbar region of the spine.

Experiments in 2D/3D image registration, in accordance with the algorithm illustrated in the flow chart in FIG. 1, and with the method of motion field generation as described above, have been carried out using patient clinical data. In one embodiment, a CT resolution of 0.87×0.87×1.00 mm (256× 256×300 voxels) has been used. FIG. 17A schematically illustrates target localization between a DRR of the target and an x-ray image of the target, in an embodiment in which the target is located within the cervical region of the spine. FIG. 17B schematically illustrates target localization between a DRR of the target and an x-ray image of the target, in an embodiment in which the target is located in the thoracic region of the spine. FIG. 17C schematically illustrates target localization between a DRR of the target and an x-ray image of the target, in an embodiment in which the target is located in the lumbar region of the spine.

In order to evaluate the image registration algorithm, the target registration error (TRE) has been computed. The TRE is computed as the difference between the displacements obtained using the fiducial-less tracking, and the displacements using fiducial tracking:

$$TRE = \sqrt{(dx-dx_0)^2 + (dy-dy_0)^2 + (dz-dz_0)^2} \quad (18)$$

FIG. 18 is a table of TRE (target registration error) values for different targets located within the cervical, thoracic, and lumbar regions, in embodiments in which fiducials are kept in the CT scan. FIG. 19 is a table of TRE (target registration error) values for different targets located within the cervical, thoracic, and lumbar regions, in embodiments in which fiducials are removed in the CT scan. As seen from FIGS. 18 and 19, the mean for the TRE is less than 0.6, using the fiducial-less tracking method and system described in the present patent.

In sum, a method and system is disclosed in this patent for enhancing an image of an object so as to increase the visibility in the image of at least one structure within the object, for example reference skeletal structures and treatment targets in an anatomical region. In one embodiment, a fiducial-less tracking method and system, based on non-rigid image registration, includes a system and method for enhancing both the DRRs (reconstructed from pre-operative scam data) and the near real time x-ray projection images. The image enhancement technique includes constructing a top-hat filter operator, configured as a weighted combination of an opening of the image with a first structural element, and a closing of the image with a second structural element, and applying the top-hat filter operator to pixels in at least two different neighborhoods within the image.

While the invention has been particularly shown and described with reference to specific preferred embodiments, it should be understood by those skilled in the art that various changes in form and detail may be made therein without departing from the spirit and scope of the invention as defined by the appended claims.

What is claimed:

1. A method of enhancing an image of an object so as to increase the visibility in the image of at least one skeletal structure within the object, wherein the image is characterized by a plurality of pixels, each pixel having an associated pixel value that represents the image intensity of a corresponding unit volume of the object, the method comprising:

generating a two-dimensional (2D) reconstructed image from a three-dimensional (3D) scan of the object, wherein the 2D reconstructed image includes the skeletal structure;

generating a 2D x-ray image of the object, wherein the 2Dx-ray image includes the skeletal structure;

for each of the 2D reconstructed image and the 2D x-ray image a) selecting at least a first neighborhood and a second neighborhood within the image, b) constructing an operator configured to select, within the first and second neighborhoods, one or more pixels having an optimal pixel value, and to eliminate the remaining pixels in the neighborhoods;

c) applying the operator to the selected neighborhoods so that only the pixels having the optimal pixel values remain in the selected neighborhoods, and the remaining pixels in the selected neighborhoods are eliminated to produce an enhanced image; and registering the enhanced 2D x-ray image with the enhanced 2D reconstructed image by deriving a transformation between a coordinate system of the enhanced 2D xray image and a different coordinate system of the enhanced 2D reconstructed image.

2. A method in accordance with claim 1, wherein the first and the second neighborhoods are characterized by different sizes.

3. A method in accordance with claim 2, further comprising the act of constructing the operator so that the operator is configured to perform the following acts:

1) select, from each neighborhood, the pixel having the largest pixel value;

2) compare the pixel selected from the smaller of the first and the second neighborhood with the pixel selected from the larger of the first and the second neighborhood; and 3) if the pixel selected from the smaller neighborhood is greater than the pixel selected from the larger neighborhood by a threshold amount, keep the pixel; otherwise, eliminate the pixel.

4. A method in accordance with claim 1, wherein the operator comprises a non-linear operator.

5. A method in accordance with claim 4, wherein the operator comprises a non-linear top-hat filter operator.

6. A method in accordance with claim 1, wherein the act of selecting the neighborhoods comprises:
selecting the at least two different neighborhoods within the image so that at least a portion of the structure within the object is included in at least one of the neighborhoods.

7. The method of claim 1, wherein the 2D reconstructed image from a 3D scan is a digitally reconstructed radiograph from a computed tomography scan.

8. An apparatus for enhancing an image of an object so as to increase the visibility in the image of at least one skeletal structure within the object, the image being characterized by a plurality of pixels, each pixel having an associated pixel value that represents the image intensity of a corresponding unit volume of the object, the apparatus comprising:

a) a neighborhood selector configured to select at least a first neighborhood and a second neighborhood within the image for each of a two-dimensional (20) reconstructed image from a three-dimensional (3D) scan of the object and a 2D x-ray image of the object, wherein each image of the object includes the skeletal structure;

b) an operator generator to construct an operator configured to select, within the first and second neighborhoods of each image, one or more pixels having an optimal pixel value, and to eliminate the remaining pixels in the selected neighborhoods; and c) a controller to apply the operator to the selected neighborhoods of each image so that only the pixels having the optimal pixel values remain in the selected neighborhoods, and the remaining pixels in the selected neighborhoods are eliminated to produce enhanced images, and to register the enhanced 2D x-ray image with the enhanced 2D reconstructed image by deriving a transformation between a coordinate system of the enhanced 2D x-ray image and a different coordinate system of the enhanced 2D reconstructed image.

9. An apparatus in accordance with claim 8, wherein the operator comprises a non linear operator.

10. The apparatus of claim 8, wherein the 2D reconstructed image from a
3D scan is a digitally reconstructed radiograph from a computed tomography scan.

* * * * *